United States Patent
Harpale

(10) Patent No.: US 8,185,412 B1
(45) Date of Patent: May 22, 2012

(54) METHOD AND APPARATUS FOR CHRONIC CARE TREATMENT CONTROL WITH CUSTOM NAMED-TYPE FACTORS AND USER ESTIMATION ERROR CORRECTION

(76) Inventor: Mahesh Harpale, Lincoln Park, NJ (US)

( * ) Notice: Subject to any disclaimer, the term of this patent is extended or adjusted under 35 U.S.C. 154(b) by 669 days.

(21) Appl. No.: 12/319,175

(22) Filed: Jan. 2, 2009

Related U.S. Application Data

(60) Provisional application No. 61/072,227, filed on Mar. 28, 2008.

(51) Int. Cl.
*A61B 5/00* (2006.01)
(52) U.S. Cl. .......... 705/3; 705/2; 128/898; 702/19
(58) Field of Classification Search ............ 702/19; 128/898
See application file for complete search history.

(56) References Cited

U.S. PATENT DOCUMENTS

| | | | |
|---|---|---|---|
| 5,822,715 A * | 10/1998 | Worthington et al. .......... 702/19 |
| 6,368,272 B1 | 4/2002 | Porumbescu |
| 6,691,043 B2 | 2/2004 | Ribeiro, Jr. |
| 7,179,226 B2 | 2/2007 | Crothall |
| 2006/0272652 A1 * | 12/2006 | Stocker et al. ............ 128/898 |
| 2007/0179434 A1 | 8/2007 | Weinert |

* cited by examiner

*Primary Examiner* — Dilek B Cobanoglu

(57) ABSTRACT

A method and apparatus to record and track patient's estimation of arbitrary factor types, to analyze response errors utilizing discrete measurements, to isolate errors in various factor types and their response correlations, to enable patient in refining factor mix to reduce estimated outcome variations, and to improve patient estimation with corrections using a continuous feedback system. The input factors for the treatment in case of a Diabetic patient may be food intake, medication, activity, stress level etc, while the treatment outcome or response may be blood glucose level that the patient needs to keep within specific limits. Present invention enables a chronic care patient, such as a Diabetic patient, to make better and informed decisions about their treatment, reduce input factor estimation errors, reduce outcome parameter variations, and improve the patient well being by better treatment control.

13 Claims, 16 Drawing Sheets

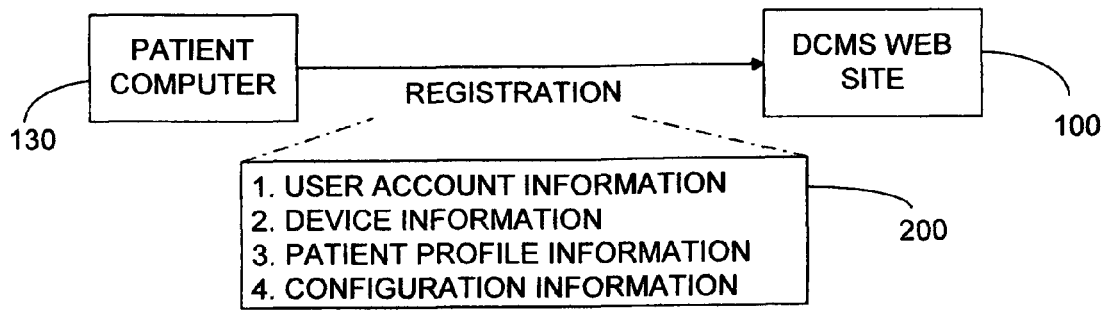
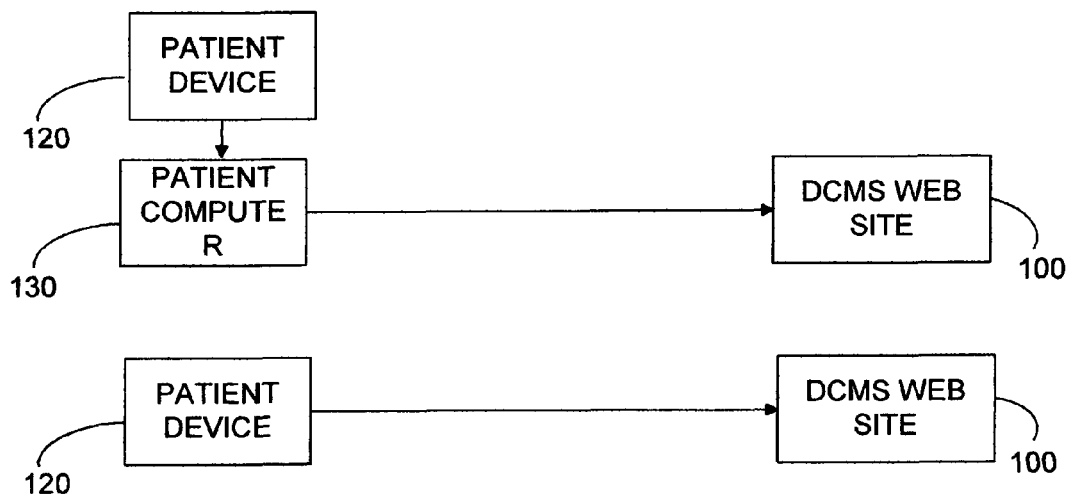
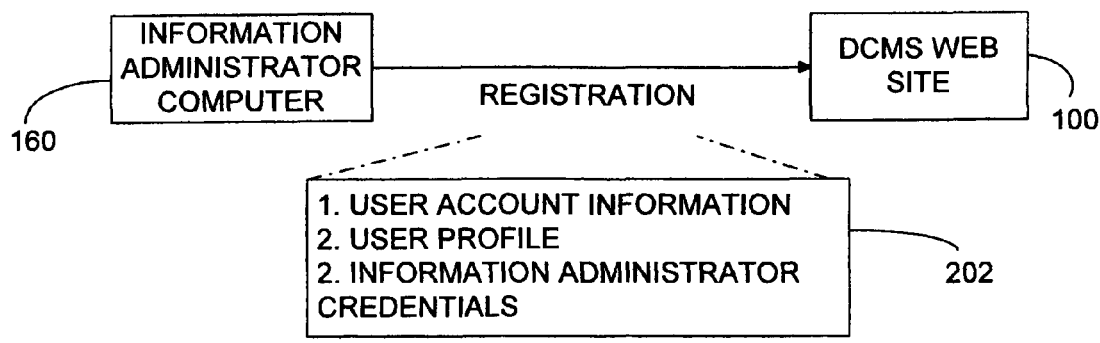

FIG. 4A
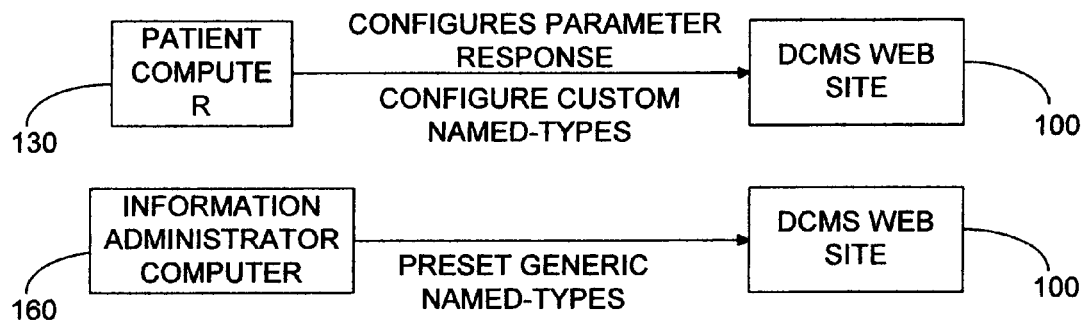
FIG. 4B
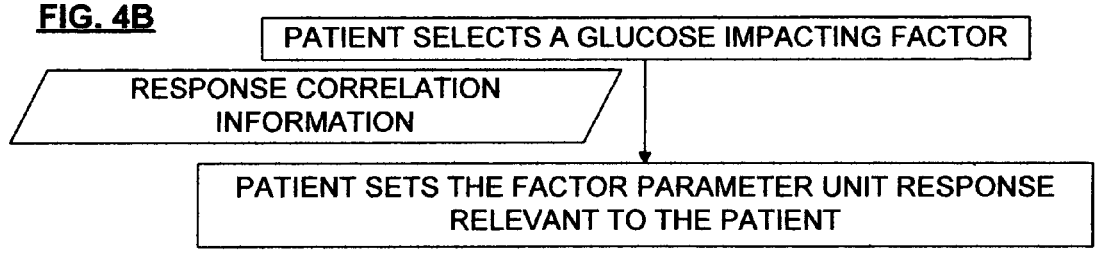
FIG. 4C
402
FACTOR [▼]
GLUCOSE RESPONSE PARAMETERS
| | PARAMETER | RESPONSE SESITITVITY |
|---|---|---|
| 1 | | |
| 2 | | |
| 3 | | |

FIG. 4G

| FACTOR | ▼ | |
|---|---|---|
| GENERIC NAMED-TYPE | ▼ | CREDENTIALS |
| BRAND | ▼ | |
| CUSTOM NAMED-TYPE | ▼ | |
| QUANTITY ☐ | UNIT ☐ | |

GLUCOSE RESPONSE PARAMETERS

| | PARAMETER | VALUE | UNIT RESPONSE | PARAMETER RESPONSE |
|---|---|---|---|---|
| 1. | | | | |
| 2. | | | | |

GLUCOSE RESPONSE VALUES

TOTAL RESPONSE

| | TIME INTERVAL | VALUE |
|---|---|---|
| 1 | | |
| 2 | | |

| FACTOR | ▼ | |
|---|---|---|
| GENERIC NAMED-TYPE 1 | ▼ | QUANTITY ☐ |
| GENERIC NAMED-TYPE 2 | ▼ | QUANTITY ☐ |

CUSTOM EVENT [▼]

EVENT SCHEDULE
DATE [    ]  TIME [    ]

NAMED-TYPES

| | FACTOR | NAMED-TYPE | UNIT QTY | EVENT QTY |
|---|---|---|---|---|
| 1. | ▼ | ▼ | | |
| 2. | ▼ | ▼ | | |

GLUCOSE RESPONSE PARAMETERS

| | PARAMETER | VALUE | UNIT RESPONSE | PARAMETER RESPONSE |
|---|---|---|---|---|
| 1. | | | | |
| 2. | | | | |

GLUCOSE RESPONSE
TOTAL RESPONSE
[    ]

| | TIME INTERVAL | VALUE |
|---|---|---|
| 1. | | |
| 2. | | |

[SAVE PRESET EVENT]

CUSTOM EVENT NAME [          ]

[SET SCHEDULE OPTIONS]

CUSTOM EVENT

PATIENT RECEIVES AN ALERT FOR BODY GLUCOSE RESPONSE CHECK
↓
PATIENT CHECKS THE ACTUAL GLUCOSE RESPONSE
↓
SYSTEM RECEIVES THE ACTUAL GLUCOSE RESPONSE INPUT

ACTUAL GLUCOSE RESPONSE

TIME OF THE GLUCOSE RESPONSE TEST
 DATE [  ]   TIME [  ]

GLUCOSE RESPONSE VALUE
 TOTAL RESPONSE
 [  ]

EXCLUDE FROM ANALYSIS ? [ ]

702

FIG. 9A
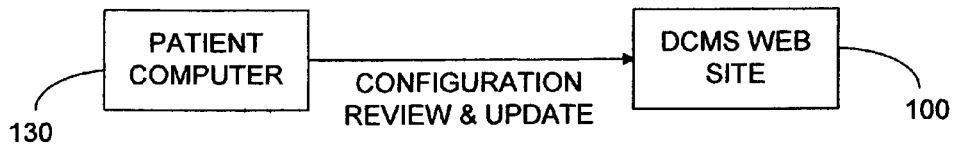
FIG. 9B
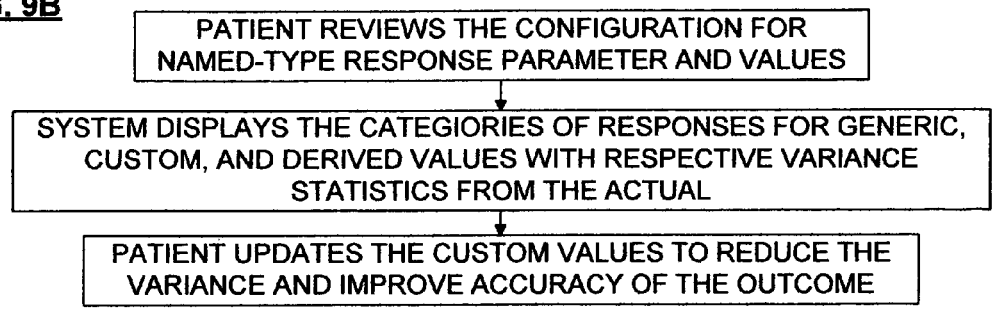
FIG. 9C
NAMED-TYPE [ ▽ ]
GLUCOSE RESPONSE PARAMETERS
| PARAMETER | GENERIC VALUE | VARIANCE | CUSTOM VALUE | VARIANCE | DERIVED VALUE | VARIANCE |
|---|---|---|---|---|---|---|
| 1. | | | | | | |
| 2. | | | | | | |
GLUCOSE RESPONSE VALUES
| | GENERIC VALUE | VARIANCE | CUSTOM VALUE | VARIANCE | DERIVED VALUE | VARIANCE |
|---|---|---|---|---|---|---|
| TOTAL | | | | | | |
| TIME INTERVAL | GENERIC VALUE | VARIANCE | CUSTOM VALUE | VARIANCE | DERIVED VALUE | VARIANCE |
|---|---|---|---|---|---|---|
| 1. | | | | | | |
| 2. | | | | | | |
902

METHOD AND APPARATUS FOR CHRONIC CARE TREATMENT CONTROL WITH CUSTOM NAMED-TYPE FACTORS AND USER ESTIMATION ERROR CORRECTION

CROSS-REFERENCE TO RELATED APPLICATIONS

This application is entitled to the benefit of Provisional Patent Application Ser. No. 61/072,227, filed 2008 Mar. 28.

STATEMENT REGARDING FEDERALLY SPONSORED RESEARCH OR DEVELOPMENT

The invention is not made under federally sponsored research and development.

REFERENCE TO SEQUENCE LISTING, A TABLE, OR A COMPUTER PROGRAM LISTING

Not applicable.

BACKGROUND OF THE INVENTION

This invention is related to the field of treatment management and control for patients with chronic care conditions, such as Diabetes, that require long-term control of specific health parameters for the patient.

The invention is explained considering Diabetes, which is a chronic and life-threatening condition. However, it should not be considered as a limitation but as an illustration of application of the invention. Diabetes has no known cure and patients need to control their blood glucose levels by lifestyle changes and/or long-term medication. Diabetes is caused by inadequate availability of or diminished response to an essential body hormone, insulin, affecting energy metabolism and resulting in serious health conditions. There are an estimated 200 million people worldwide suffering from diabetes, with US alone accounting for 18 million patients. The current treatment involves controlling the blood glucose in the appropriate levels by drugs, diet, and exercise regimen. Uncontrolled blood glucose levels cause many complications such as blindness, kidney failure, heart disease, neuropathy, and poor circulation causing amputations. Total costs of Diabetes including costs of associated complications are estimated at $92 billion in US. Primary cause of complications associated with Diabetes treatment is due to high variability in blood glucose control.

With the solutions and techniques available in the market today, a Diabetic patient needs to take insulin response enhancement drugs or take insulin or insulin type drugs to control their blood glucose levels in the appropriate range. There are several internal and external factors that affect a patient's blood glucose levels such as metabolic processes, food intake, physical activities, stress levels etc. So along with medication, patient needs to control these factors closely. With the current available techniques, to manage the blood glucose level within appropriate ranges, a patient needs to understand impact of these factors and manage them on a continual basis, making constant decisions about the impact of these various factors.

In a typical solution, for impact of food intake, a patient needs to understand and estimate carbohydrate count for all types of food and determine the insulin that the patient must administer to keep it in the appropriate range. In another solution, the patient must determine the strength and impact of various activities that the patient may undertake along with carbohydrate counting and understanding glycemic index of the food. Also, the patient must determine the metabolic response and resulting change in blood glucose levels for unit levels of these factors to determine the overall glucose level change. Adding to the complexity the factors may be interdependent and may affect the patient's metabolic response to varying degrees. For example, in different types of illnesses, the estimated impact of a unit level of food, activity metabolic responses may alter and patient needs to account for that to correctly control the blood glucose level. These create complex scenarios for which the patient needs to make estimations introducing errors in estimations and variations in blood glucose control. U.S. Pat. No. 6,691,043 to Rebeiro (2004) discloses a bolus calculator for Diabetic patients to calculate a larger amount of amount of insulin (bolus) when food is ingested or in response to correct blood glucose level higher than prescribed level is observed. However, the patient is making a repetitive estimate about the amount carbohydrates that becomes a critical weak link introducing calculation errors, as patient has no systematic and accurate basis to calculate amount of carbohydrates in any arbitrary or custom food that the patient may ingest. Similarly, U.S. Pat. No. 6,368,272 to Porumbescu (2002) discloses a method to make predictions regarding how a person's biological system will respond to a series of stimuli. It utilizes ongoing information from the user-patient and a time function describing dynamic characteristics of the input to predict ongoing metabolic status. However, here also, the patient makes the estimates about the input information such as food intake, activities etc. and is not provided with a consistent and reliable basis to make such estimates. In addition, use of time functions to create mathematical models in predicting metabolic response and calculation of corrective action such as required amount of Insulin (bolus) creates a much higher level of complexity. This also creates a difficulty in communicating such complex models to the patient. Furthermore, it attempts to improve predictions by improving the mathematical models whereas the input information, on which the mathematical models rely, itself may be erroneous.

In yet another solution, an attempt has been made to create databases of standard types of food giving carbohydrate counts, glycemic index or databases of standard activities giving calories burnt that may somewhat help the patient make better estimates. However, a patient hardly faces standard type of activities or foods in the patient lifestyle. Also even with standardized factor types, the patient still needs to make an estimation of portion or strength of the factor as in strength of standard exercise routine or portion of food. U.S. Pat. No. 7,179,226 to Crothall (2007) discloses a method to compute recommended dosage intake taking into consideration variables such as blood glucose level, activity, meals, etc. It utilizes one or more reference databases such as food database containing USDA food nutrition facts or an activity database containing list of common sports activities and the calorie burn ratios to allow user to select from these common food items or activities and calculate recommended dosage. However, it does not take into account the typical case when patient encounters non-standard factors such as food items or activities. It does not provide a mechanism to the patient to estimate and track such arbitrary, or ad-hoc, or custom factor types. So the issue of patient making erroneous estimates about these arbitrary factor types remains. Not only for arbitrary factor types but also for common factor types, the prior art needs input from the patient about the relative portion of the food item or the relative strength of the activity and that may not be accurate. It does not take into account the fact that the patient input may be erroneous and provides no mechanism to the patient to improve or correct the estimates.

There are solutions being introduced to develop a closed loop feedback system where glucose response can be continuously monitored and any out of control changes can be fed back into a system that will administer medication to bring the blood glucose level back in control. However, there is an inherent latency between body's response to medication or any factor, per say. So any glucose response corrections in such an automated or closed loop system may come later than when needed and also more than needed due to the latency factor, introducing further variations in blood glucose control.

There are several shortcomings in glucose control techniques available today. These create outcome variations and affect treatment effectiveness resulting in risk of serious and costly health complications. Many of the issues that a patient typically encounters with solutions and techniques available today are:

a) A patient is encumbered with making repetitive estimates about the treatment parameters, especially with making estimates about relative strengths of factors such as carbohydrate counts or relative portions of food. This introduces human errors and results in variations in glucose control. Typical factors that patient experiences are arbitrary and non-standard. A patient cannot form a consistent basis to form these estimates accurately. Patient lifestyle is complex and the patient faces mix of input factors that makes it even harder for patient to not only estimate expected change in glucose response but also isolate errors and correct them for a particular factor type. Even smaller mistakes in input parameter estimates create cumulative response variations and over a long-term may have serious impact on patient health.

b) A patient may make mistake not only estimating strength of the input factor but also glucose response sensitivity to input factor. Resulting change in glucose response depends on both strength and sensitivity of input factors. It is hard for the patient to isolate and correct these errors manually. Adding to the complexity is the fact that a patient is not only faced with multiple factors like a mix of physical activities, emotional stress, and ingestion of a few food types, but also that the impact of these factors may be positive or negative, that is augmenting or canceling the errors. So, it becomes a highly complex scenario for a patient to isolate and correct these errors.

c) Each factor type may have a varying impact on the glucose level with different lengths of time. Medications such as Insulin, physical activities such as exercise regime, or oral glucose tablets may be just different types of corrective factors that a patient may need to consider to counteract and keep resulting glucose level under control. So, with a complex mix of factors or with a varying impacts of input factors, a complex counteractive action may be needed by a patient such as different mix of Insulin types or mix of other counteracting factors. With such complex scenarios, patient may not be able to judge and determine the most appropriate corrective action.

d) Since, a patient cannot accurately determine the most appropriate action needed to correct the estimation errors, the patient may make mistakes in corrective steps. This further compounds the problem and complicates correcting the errors.

e) A glucose response is not only affected by specific factors, but also by circumstantial changes such as aging, lifestyle alterations, or sudden unforeseen changes. These changes may be gradual and/or complex for patient to correlate to the response changes manually and hence hard to estimate.

f) Standardized databases of factors such as food, activities etc are insufficient to address arbitrary factors that a patient faces in a practice. Also, even with standardized databases, patient still needs to make estimates about the relative portions or strengths of these factors. With the solutions available today, these errors result into response variations and there is no mechanism for a patient to track, isolate, and address these errors consistently.

g) Static reports that allow a patient to analyze treatment outcomes are insufficient for the patient to isolate the errors. They depict observed response, events, and influencing factors at different time intervals; however they do not track and isolate estimated response for arbitrary factor type. These report fail to accurately correlate individual trackable factor type with the observed response. So, the patient has no consistent way to analyze errors against a particular factor type. Also they neither take into account separately factor type strength and sensitivity nor do they track corrective responses separately. So, the corrective responses can result into further errors, compounding the overall problem.

h) The estimation errors may not only be in total response to a particular factor, but also in responses at different intervals of time. For example a patient's total response to a food type may be accurate but it may be higher than estimated in the beginning and vice a versa. There are no mechanisms available for a patient to isolate and track these errors response for arbitrary food types at different time intervals and may result in significant deviations in response at various time intervals. There are no solutions available that enable patient analyze discrete response measurements at a particular time interval against discrete response measurements of response influencing factors to correct any estimation errors.

Currently, there are no solutions that address the above-mentioned problems and shortcomings.

BRIEF SUMMARY OF THE INVENTION

Present invention gives a method and apparatus that addresses above-mentioned problems and shortcomings. Object of the invention is to assist a chronic care patient, such as a Diabetic patient, in making better and informed decisions about their treatment, and to improve the patient well being by better treatment control.

Present invention when implemented increases efficiency and effectiveness of chronic care treatment such as blood glucose control for Diabetic patients. Specifically in Diabetic patients, reduced blood glucose level variations and improved glucose level control significantly reduce patient's risk of developing costly and potentially life-threatening complications. The invention enables the patients to attain a better treatment control by reducing variations in the controlled parameter like blood glucose level for Diabetes patients. There have been advances in Diabetes control drugs and drug administration techniques; however, with today's solutions the patient is still encumbered with making input estimates for treatment parameters that may contain errors. This creates a crucial weak-link in the effectiveness of the treatment. Present invention addresses this weak link by providing a solution to the patient to improve estimation and reduce errors due to incorrect estimates. The input factors for the treatment in case of a Diabetic patient may be food intake, medication, activity, stress level etc, while the treatment outcome or response may be blood glucose level that the patient needs to keep within specific limits.

Present invention comprises a method and apparatus to record and track patient's estimation of arbitrary factor types, to analyze response errors utilizing discrete measurements, to isolate errors in various factor types and their response correlations, to enable patient in refining factor mix to reduce estimated outcome variations, and to improve patient estimation with corrections using a continuous feedback system. The terms arbitrary, ad-hoc, and custom are used to indicate factors or factor types that are relevant for the patient and may or may not be relevant for a general population. The present invention not only addresses the issue of patient estimation errors but also enables the patient to lead a flexible lifestyle catering to a random mix of arbitrary or custom factor types that are relevant to the patient. It enables patient or patient's healthcare administrator to form a consistent and reliable basis to analyze and correct errors or variations in treatment outcome and improve patient health.

Accordingly, several objects and advantages of the present invention are:

(a) to provide the patient or patient's healthcare administrator a mechanism to estimate input parameters and their strengths for ad-hoc or arbitrary factor types creating named factor types or named-type factors;

(b) to provide the patient a mechanism to improve the estimation by isolating responses to named factor types and correlating response variations to errors in named factor type inputs or their parameter inputs;

(c) to provide the patient a mechanism to improve the estimation by distinguishing and isolating errors between strength and response sensitivity of named factor types (d) to provide the patient a mechanism to improve the estimation by distinguishing and isolating errors between for a mix of input factors;

(e) to provide the patient a mechanism to improve the estimation by isolating responses to factor type parameters, or mix of different composition factor types and form a consistent and reliable basis for estimating response to factor types;

(f) to provide the patient a mechanism to refine reduction in outcome variance against the treatment parameters to by allowing to review the estimated response and adjust the inputs;

(g) to provide the patient a mechanism to refine reduction in outcome variance against the treatment parameters by allowing to use response estimation at total as well as different time intervals;

(h) to provide the patient a mechanism to refine reduction in outcome variance against the treatment parameters by allowing to choose a mix of input factor types;

(i) to provide the patient a mechanism to adapt the treatment to patient's lifestyle by allowing the patient to choose available input factor type and the system to identify most appropriate mix of inputs amongst those selected by the patient;

(j) to provide the patient a mechanism to reduce estimation errors due to circumstantial changes by utilizing a continuous feedback system and statistical correction mechanism such as rolling estimate averages;

(k) to provide the patient a mechanism to choose named factor types from 3rd party resources that may be consistent with patient's needs;

(l) to provide the patient a mechanism to prevent any input errors by utilizing automated recognition means such as electronic recognition of standard or branded named factor types;

(m) to provide the patient's healthcare administrators a mechanism to clearly understand and analyze the basis of patient estimations, resulting response, and any improvements needed for effective treatment control.

Still further objects and advantages will become apparent from a consideration of the ensuing description and drawings.

BRIEF DESCRIPTION OF THE SEVERAL VIEWS OF THE DRAWING

In the drawings, closely related figures have the same number but different alphabetic suffixes. These and other features and advantages of the invention will now be described with references to the drawings of certain preferred embodiments, which are intended to illustrate and not to limit the invention, and in which:

FIGS. 2A-2F illustrate the registration function for various types of entities and their interaction to fulfill the function. FIGS. 2A and 2B illustrate the process for Patient registration function, FIG. 2C illustrates the process for Information Administrator registration function, and FIGS. 2D-F illustrate the process for Healthcare Professional registration function.

FIG. 3A and FIG. 3B illustrate the process, while FIG. 3C depicts an example of a user interaction (UI) screens for the factor parameter setup function.

FIGS. 4A-4H illustrate the function for creating and configuring arbitrary or custom named factor types. FIG. 4A illustrates the components interacting in the process for creating custom named factor types, FIG. 4B illustrates the process, and 4C depicts an example of a UI screen for configuring glucose response to various glucose response parameters for the patient. FIG. 4D illustrates the process for third party information administrators to configure preset generic and branded named factor types and FIG. 4E shows an example of a UI screen for the same. FIGS. 4F and 4G show the process flow and an example a UI screen, respectively, to illustrate the process of custom named factor type setup by the patient. FIG. 4H shows an example of a UI screen modification for combination of generic named-types as a basis for a custom named-type.

FIGS. 5A-E illustrate the function for creating and configuring custom events. FIGS. 5A-C illustrate the components and process for creating an ad-hoc and a preset custom event for the patient. FIGS. 5D and 5E show an example of a UI screen to create an ad-hoc and a preset custom event respectively.

FIG. 6A illustrates the process flow for analysis of a custom event to improve the outcome of an estimated response. FIGS. 6B-6C show an example of a UI screen to perform such analysis. FIGS. 6D-6E illustrates process flow for setting up alert ranges, alerts for indicating estimated or actual response that cross alert range limits, and searching for the matching corrective named factor types. FIG. 6F shows an example of a UI screen.

FIGS. 7A, 7B, and 7C illustrates the components, the process flow and an example of a UI screen respectively.

FIGS. 8A and 8B illustrate the component interactions and the process flow respectively, while FIGS. 8C and 8D show a hypothetical example of a derived response for a named factor type using an illustrative method.

FIGS. 9A-C illustrate the function for Configuration Adjustments. FIGS. 9A, 9B, and 9C illustrates the components, the process flow and an example of a UI screen respectively for patient configuration adjustments.

REFERENCE NUMERALS IN DRAWINGS

Figure 1A:
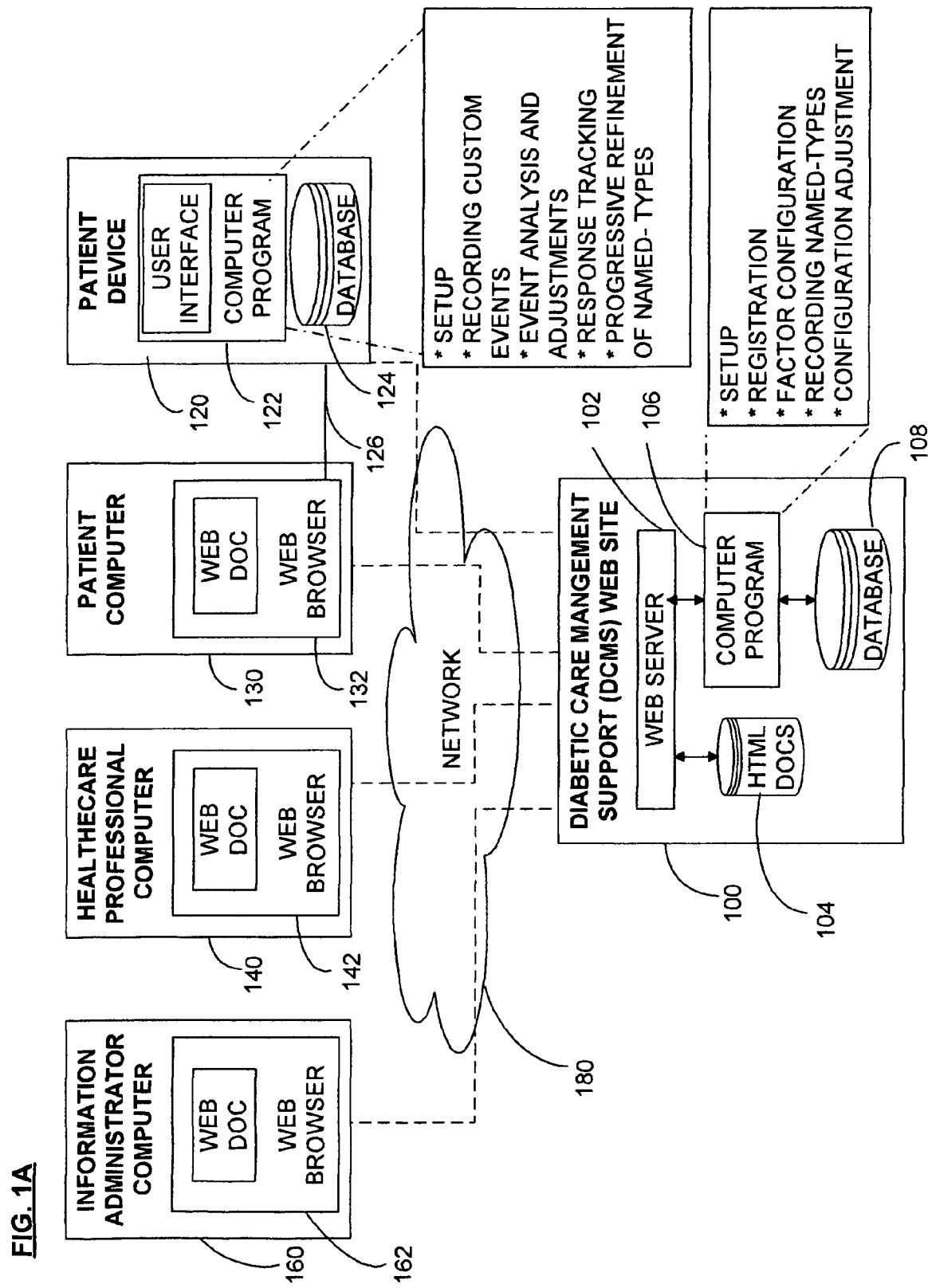
FIG. 1A is a high level architectural illustration of the primary components of a system that operates according to the present invention.

In the drawings, the first digit of each reference number indicates the Figure number in which the referenced item first appears.

- 100—Diabetic Care Management Support Web site, referred hereafter as DCMS Web site.
- 102—Web server at DCMS Web site 100, referred hereafter as DCMS Web server.
- 104—HTML documents at DCMS Web site 100.
- 106—computer program for processing requests at DCMS Web site 100.
- 108—database to store information at DCMS Web site 100.
- 120—portable programmable computing device used by patient, referred hereafter as patient-device.
- 122—computer User Interface (UI) at patient-device 120, referred hereafter as patient-device-UI.
- 124—database to store information at patient-computer 130.
- 126—standard network connector between patient-device 120 and standard computer used b the patient 130.
- 130—standard computer used by patient, referred hereafter as patient-computer.
- 132—standard Web browser at patient-computer 140, referred hereafter as patient-browser.
- 140—standard computer used by HealthCare Professional (HCP), referred hereafter as HCP-computer.
- 142—standard Web browser at HCP-computer 140, referred hereafter as HCP-browser.
- 160—standard computer used by Information Administrator (IA), referred hereafter as IA-computer.
- 162—standard Web browser at IA-computer 160, referred hereafter as IA-browser.
- 180—standard network connecting computers and computing devices.
- 200—details of information required by DCMS Web site 100 for patient registration.
- 202—details of information required by DCMS Web site 100 for Information Administrator (IA) registration.
- 204—details of information required by DCMS Web site 100 for HealthCare Professional (HCP) registration.
- 206—token transferred from DCMS Web site 100 to HCP-computer 140.
- 302—an example of a User Interface (UI) screen for setting glucose response factors.
- 304—an example of a User Interface (UI) screen for setting glucose response parameters.
- 402—an example of a User Interface (UI) screen for setting glucose response parameters.
- 404—an example of a User Interface (UI) screen for setting glucose response parameters.
- 406—an example of a User Interface (UI) screen for creating a custom named factor type.
- 408—an example of a User Interface (UI) screen modification for using combination of generic named factor types to create a custom named factor type.
- 502—an example of a User Interface (UI) screen for creating custom event comprising one or more custom named factor types.
- 504—an example of a User Interface (UI) screen for creating preset custom events.
- 602—an example of a User Interface (UI) screen for custom event analysis.
- 604—an example of a User Interface (UI) screen for custom event adjustments improving the outcome of an estimated event response.
- 606—an example of a User Interface (UI) screen for selecting matching named factor type as a corrective measure in improving an estimated event response.
- 702—an example of a User Interface (UI) screen for submitting actual event response.
- 902—an example of a User Interface (UI) screen for configuration adjustments for a custom named factor type

DETAILED DESCRIPTION OF THE INVENTION

To facilitate a complete understanding of the invention, the description of the preferred embodiment is arranged within the following sections:
GLOSSARY OF TERMS AND ACRONYMS
COMPONENT DESCRIPTION AND OPERATION
ADVANTAGES

GLOSSARY OF TERMS AND ACRONYMS

The following terms and acronyms are used throughout the description:

Client-Server: A model of interaction in a distributed system in which one program sends a data-processing request to another independent program. The requesting program is called the "client", and the program that responds to the request is called the "server".

Network: An interconnection of a group of computers and computing devices that may be connected with each other using technologies like a network cable or wireless transmitter-receiver.

Internet: A collection of interconnected (public or private) networks that are linked together by a set of standard protocols. Internet allows two computers on two disparate networks to connect and send requests to each other.

Intranet: Intranet is a sub-type of Internet where internal networks are connected together and only internal people from the organizations have access. Outside people cannot access Intranet.

Extranet: Intranet is a sub-type of Internet where internal networks are connected together with a link to the outside trusted networks and internal people from the organizations as well as alliance partners have access. General public cannot access Intranet.

Portable Computing Device (Mobile Device, Handheld Device, Personal Digital Assistant, PDA, Smart Device): A smaller sized portable computing device, typically comprising a small visual display screen for user output or user interface (UI) and a miniature keyboard or a touch screen for user input.

World Wide Web ("Web"): A distributed collection of inter-linked, user-viewable hypertext documents (commonly referred as Web documents or Web pages) that are accessible via the Internet. It is also used herein to refer to the client and server software components, which provide user-access to such documents using standardized Internet protocols.

Web Site: A computer system that serves informational content over a network using the standard protocols of World Wide Web. Typically, a Web site corresponds to a particular Internet domain name, such as "google.com". As used herein, the term is generally intended to encompass the hardware/software server components that server the informational content over the network Web Server: Web server is a software component of a Web site that accepts HTTP requests and serves informational content with the help of static HTML documents or other software components helping to create dynamic HTML documents or combination of both.

Web Browser: Web browser is a software component at the client side that accesses the informational content from Web server. Broadly, Web browser accesses informational content and renders it on the client screen.

HTTP (Hyper Text Transport Protocol): The standard World Wide Web client-server protocol used for the exchange of information. HTTP includes a number of different types of messages that can be sent from the client to the server to request different types of server actions. HTTP GET request sends a message to server to access a document. HTTP POST request sends a message to server to process data and includes data in the message.

HTML (Hyper Text Markup Language): A standard coding convention and fixed set of codes for attaching presentation and linking attributes to informational content within documents.

CGI ("Common Gateway Interface"): A standard for running external programs at Web server that typically generates a dynamic response to the browser's request.

Web Server Plug-in ("Plug-in"): Standard extension to the Web server that allows a request to be served dynamically by executing a set of server side instructions.

Application Server: Computer application that accepts requests from the user, accumulates data from various server side applications, formats it suitable for the user interface, and sends the data back to end-user. In web application scenario, application server works in conjunction with web server and accepts request, and provides the formatted data to web server.

CD-ROM: Compact Disc that contains data accessible by a computer. These can also be recordable and can be portable storage of data.[1]

Body Glucose Response (Glucose Response, Blood Glucose Level, Glycemia): Concentration of glucose in blood typically expressed in milligrams per deciliter (mg/dl) or millimol per deciliter (mmol/dl) influenced by many physiological processes. Blood glucose is used by cells to create energy and is identified to be maintained in an acceptable range for human body to function properly.[1]

Glycemic Index: A ranking system for carbohydrates based on their effect on blood glucose levels.[1]

Insulin: A necessary animal hormone secreted by groups of cells within the pancreas called islet cells. Most cells of the body have insulin receptors that bind the insulin in the circulation. When a cell has insulin attached to its surface, the cell activates other receptors designed to absorb glucose (sugar) from the blood stream into the inside of the cell. Without insulin, many of our cells cannot access the calories contained in the glucose very well without the action of insulin.[1]

Diabetes: Those who develop a deficiency of insulin must have it replaced via shots or pumps (Type 1 Diabetes). More commonly, people will develop insulin resistance (Type 2 Diabetes) rather than a true deficiency of insulin. In this case, the levels of insulin in the blood are similar or even a little higher than in normal, non-diabetic individuals.[1]

Novolog®: Insulin aspart marketed by Novo Nordisk a fast acting insulin analogue.[1,2]

Tae Bo®: An aerobic exercise routine developed by tae kwon do practitioner Billy Blanks.[1,3]

Tropicana Pure Premium®: Brand for an orange juice developed and marketed Tropicana Products, Inc.[4]

Minute Maid®: Brand for an orange juice developed and marketed The Coca-Cola Company.[5]

Positive Glucose Response: Response on Blood Glucose Levels to increase.

Negative Glucose Response: Response on Blood Glucose Levels to decrease.

Analysis of variance (ANOVA): A collection of statistical models, and their associated procedures, in which the observed variance is partitioned into components due to different explanatory variables.[1]

Basal Insulin: A minimal level of insulin necessary for health or life, which represents a low and continuous dosage of insulin, intended to "cover" the glucose output of the liver[1].

Bolus Insulin: A dosage of fast-acting insulin taken by a Diabetic patient with a meal intended to cover the glucose output from the meal[1].

[1]—A definition reference from Wikipedia, The Online Free Encyclopedia, "http://www.wikipedia.com".
[2]—Novolog® is a registered trademark of Novo Nordisk A/S.
[3]—Tae Bo® is a registered trademark of BG Star Productions, Inc.
[4]—Tropicana Pure Premium® is a registered trademark of Tropicana Products, Inc.
[5]—Minute Maid® is a registered trademark of The Coca-Cola Company.

COMPONENT DESCRIPTION AND OPERATION

Figure 1B:
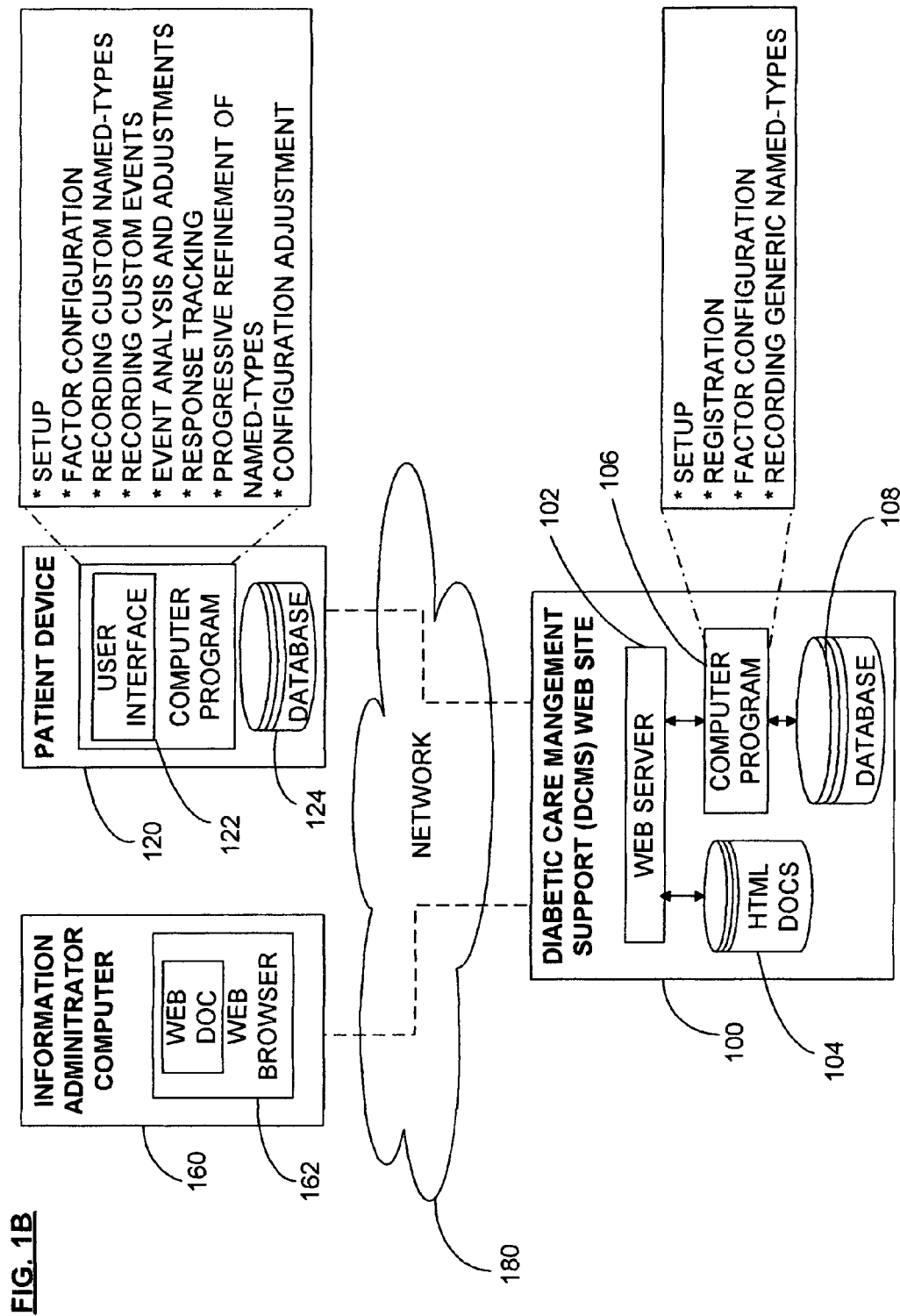
FIG. 1B illustrates an alternate arrangement of the high level architecture of the system that operates according to the present invention.

FIG. 1A illustrates a general architectural drawing of the primary components of a system that operates according to the present invention. The system may include a DCMS Web site 100, a patient-device 120, a patient-computer 130, an HCP-computer 140, and an IA-computer 160 all linked together by the network 180. The patient-device 120 may be connected with the patient-computer 130 by a network connection 126. Alternatively, as FIG. 1B illustrates, the system may include a DCMS Web site 100, a patient-device 120, and an IA-computer 160 linked together by the network 180. The patient-device 120 may connect with HCP-computer 140 or the network 180 using different networking mechanisms such as network cable or wireless connection. Alternatively, patient device 120 may be used independently with network connections made only during the periods of data transfer or synchronization using a patient-computer 130 that may have been connected on the network 180 or using a transferable data storage device such as CD-ROM or data storage diskettes.

DCMS Web site 100 is a server including DCMS Web server 102, HTML documents 104 for user interface, computer program 106 for data processing, and a database 108 for data storage. Patients, HealthCare Professionals, and Information Administrators may use patient-computer 130, HCP-computer 140, and IA-computer 160 respectively to interact with DCMS Web site 100. Patients may also use patient-device 120 to connect with DCMS Web site 100. To request any information from DCMS Web site 100 users may send an HTTP GET request to DCMS Web server 102, while to submit any information users may send HTTP POST request to DCMS Web server 102. DCMS Web Server 102 is an HTTP server that may accept a user request and generate a response to be sent back to the user. It may generate the response using HTML documents 104 and/or using a computer program 106. HTML documents 104 provide the static information content while computer program 106 does data processing and provides dynamic information content. Computer program 106 may be either a CGI application or a Web server plug-in or an application server. Patient-device 120, patient-computer 130, HCP-computer 140, and IA-computer 160 may be any type of computing device that may allow a user to access a network using a Web browser or Web enabled User Interface (UI). Patient-device 120 may include a computer program 122 that processes data and uses a database 124 to store data. The computer program 122 may use a User Interface (UI) to display output information to a user and receive input information from a user. Patient-computer 130, HCP-computer 140, and IA-computer 160 may include a Web browser 122, a Web browser 142, and a Web browser 162 respectively for receiving, processing and displaying information to a user. The browser can be any type of standard Web browser.

DCMS Web site 100 may provide functionality for allowing patients, healthcare professionals, and information administrators to register unique accounts as users for operating various functions made available on the site. Users may use various computing devices to network with DCMS Web site 100 to operate various functions on the Web site. Users seeking convenience may further use portable or handheld computing devices to interact with DCMS Web site 100. Data exchanges between such computing devices may be done on-line, that is data exchanged with direct connection using mechanisms like a network, or off-line, that is data exchanged without direct connections using various mechanisms one example being a data storage diskette. Various functions that are illustrated here may be performed in a different combination on various components. For example, FIG. 1A illustrates one of such distributions where computer program 106 performs functions of Registration, Factor Configuration, Recording Named Factor Types, Configuration Adjustment, while computer program 122 performs the functions of Recording Custom Events, Event Analysis and Adjustments, Response Tracking, Progressive Refinement of Named Factor Types. Named factor types are referred hereafter as named-types. FIG. 1B illustrate example of a different distribution with computer program 106 performs functions of Registration, Factor Configuration, Recording Generic Named Factor Types, while computer program 122 performs the functions of Factor Configuration, Recording Custom Named-Types, Recording Custom Events, Event Analysis and Adjustments, Response Tracking, Progressive Refinement of Named-Types, Configuration Adjustment. Also, those knowledgeable in the art can recognize that functions performed by Web browsers on various computing devices can also be performed by a custom computer program on that computing device capable of performing the illustrated functions in different combinations, as might be with patient-computer 130, HCP-computer 140, and IA-computer 160.

FIG. 1A illustrates arrangement of components that will fulfill various functions of the invention. As illustrated in FIG. 1A, an information administrator, a healthcare professional, and a patient may use IA-computer 160, HCP-computer 140, and patient-computer 130 to interact with DCMS Web site 100 respectively. A patient may use a patient-device 120 separately to connect with patient-computer to synchronize data with DCMS Web sire 100, while utilize it independently to fulfill some of the standalone functions that might be carried out by computer program 122. Patient device may utilize database 124 to store the data locally on the device and synchronize it periodically with DCMS Web sire 100. FIG. 1B illustrates a possible another arrangement in which patient-device 120 may interact directly with DCMS Web sire 100 synchronize the data or any computer program updates without use of patient-computer 130. Patient-device 120 may work connecting with DCMS Web sire 100 in various possible modes, examples being real-time mode where information is synchronized instantaneously, periodic mode where information is synchronized periodically, and on-request mode where information is synchronized on request from the patient. FIG. 1A also illustrates an arrangement where a healthcare professional may assist a patient in configuring, analyzing, or operating on information by using HCP-computer 140 to connect with DCMS Web sire 100 and interact with information for the patient as stored on DCMS Web sire 100. In yet another arrangement, a healthcare professional may be able to use patient-device 120 to access its information uniquely to assist the patient in configuring, analyzing and set up.

As described earlier, a patient may use patient-device 120 independently and may receive data feeds from the DCMS Web Site 100 only on a need basis. A patient may also use patient-device 120 interacting with DCMS Web site 100 directly or via patient-computer 130 using different communication mechanisms one example being standard network connector 126. A patient may setup patient-device interactions with other computing devices for data synchronization or operational updates using computer-program 122, Web browser 132 and computer program 106, together or separately. In one of the possible mechanisms, a patient may use patient-computer 130 to register custom information with DCMS Web site 100 that may include registration information 200 such as a unique identification, device information, patient's profile information, and various configuration parameters that may decide operating choices for the device. FIGS. 2A and 2B illustrate these components of a registration function. In another mechanism, a patient may use patient-device 120 interacting directly with DCMS Web site 100 for the registration function. FIG. 2B illustrates the components of two of these mechanisms. Please, note that even though illustrations depict one of the mechanisms using patient-computer 130 to perform different functions, they might also be performed directly by patient-device 120 as explained in FIG. 2B.

Figure 2D:
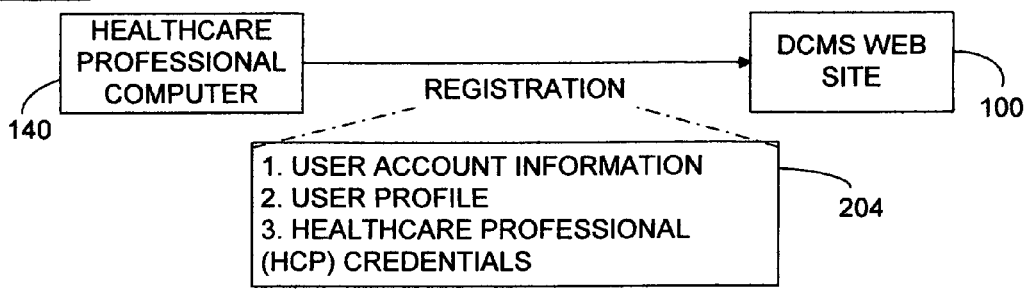
Figure 2E:
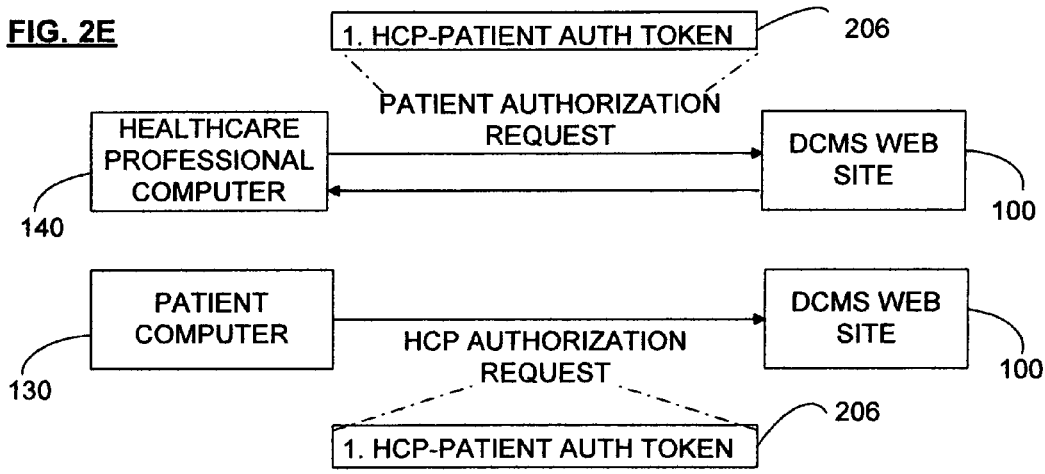
Figure 2F:
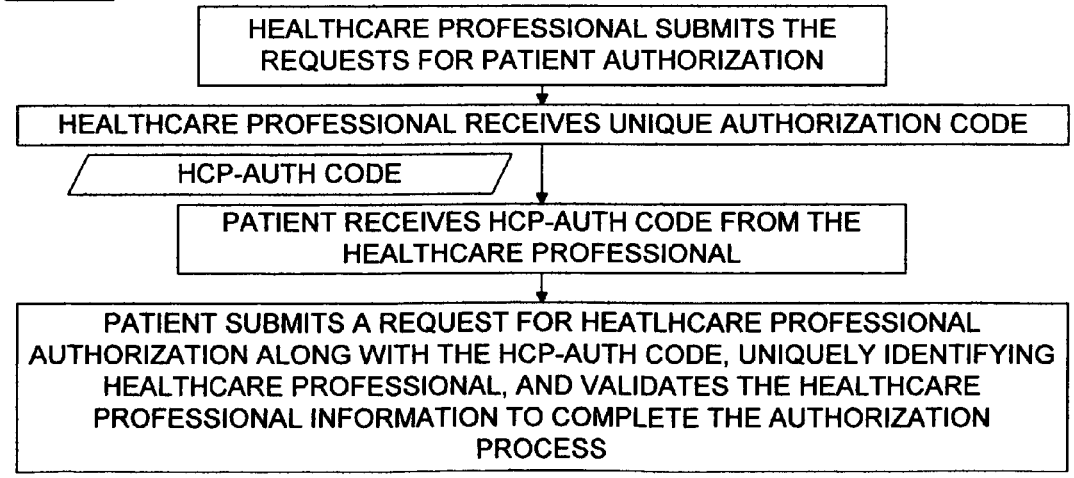

FIG. 2C illustrates that an information administrator may use IA-computer 160 to register custom information with DCMS Web site 100 that may include registration information 202 such as a unique identification, profile information, and information administrator credential information. Multiple information administrators may register with their custom information. An information administrator may include administrator for DCMS Web site 100 or various third party administrators from representative organizations like healthcare or information research institutes, government organizations, or various product or brand owners for factors that influence a body glucose response. Similarly, a healthcare professional may register with DCMS Web site 100 as illustrated in FIG. 2D. Healthcare professional may register custom registration information 204 that may include unique account identification, profile information, and professional credentials. A healthcare professional (HCP) may use HCP-computer to assist a patient in set-up, analysis, or change of the patient's account information on DCMS Web site 100. Information on DCMS Web site 100, may then be updated on patient-device 120 using various synchronization mechanism described earlier. A healthcare professional may use a unique account on patient-device 120 to also perform various functions such as setup, analysis, or change. A patient may authorize a healthcare professional to access patient's account on DCMS Web site 100 or patient-device 120. Once authorized, HCP may access a patient's information using HCP's account and assist the patient with setup, analysis, or change. FIGS. 2E and 2F show example of process for such authorization. As illustrated in FIG. 2E HCP may receive HCP-Patient authorization token 206 from DCMS Web site 100 uniquely identifying requesting HCP. There may be many forms this token, an example being an encrypted electronic identification number or an encrypted identification electronic document. Patient may receive this unique token from HCP and submit a request for HCP authorization using patient-computer 130 or patient-device 120 to DCMS Web site 100. DCMS Web site 100 may show unique profile information for HCP such as name and office location for patient to uniquely identify HCP. Upon successful identification and information access authorization of HCP by the patient, DCMS Web site 100, may allow authorized HCP to access information for the patient using HCP's account. FIG. 2F shows the example of this process flow.

Figure 3A:
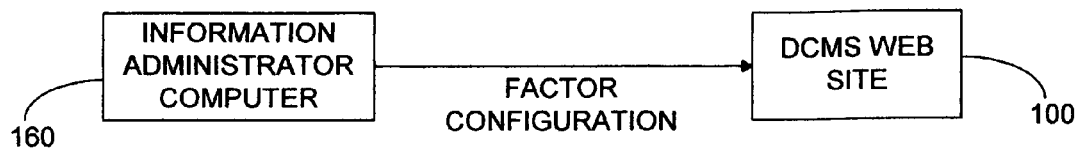
FIGS. 3A-3C illustrate the parameter setup function for various glucose-impacting factors.
Figure 3B:
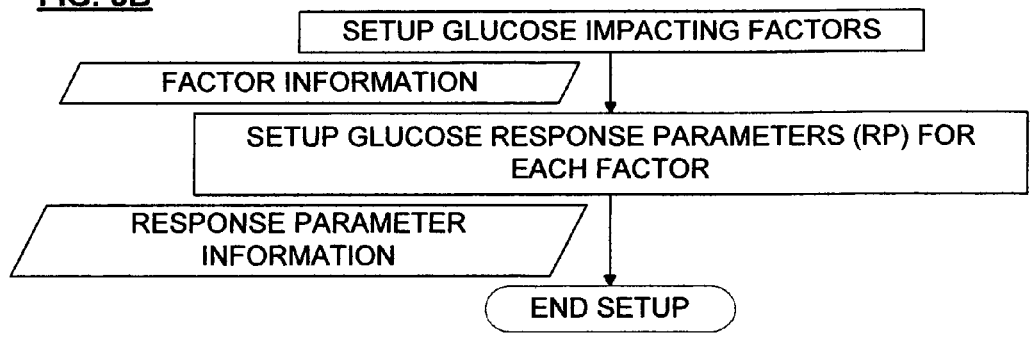
Figure 3C:
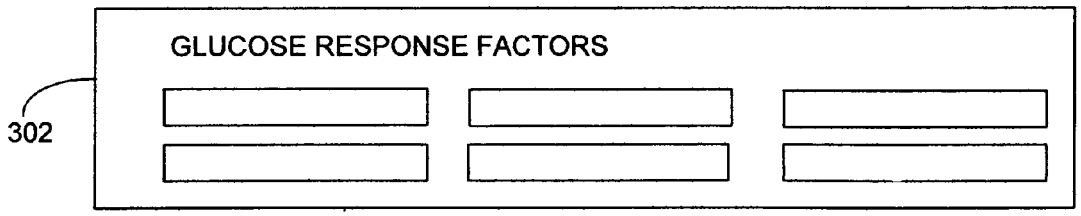
Figure 3C:
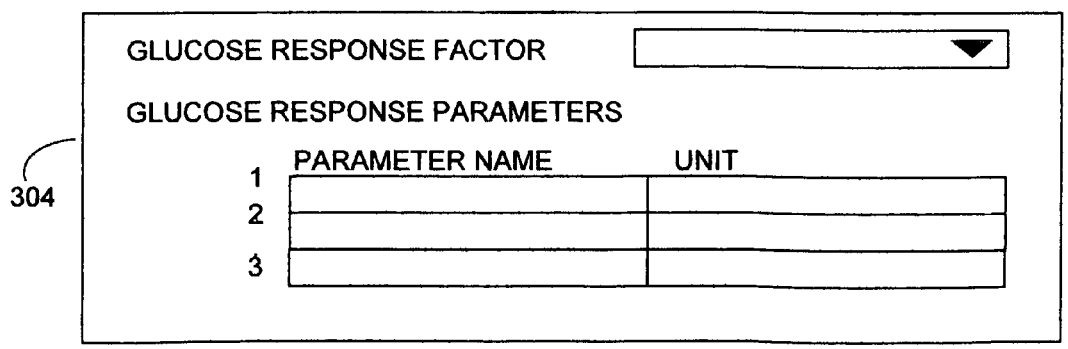

Information administrator may use IA-computer 160 to setup different factors that impact glucose response for a patient. This information may be used as common setup information for a patient. A patient may also setup or change such information for the patient using patient-device 120 or patient-computer 130 or a healthcare professional may also setup or change this information for the patient. FIGS. 3A and 3B illustrate the components and process flow for this factor configuration function. Information administrator may input various factors that impact glucose response of a person. Few of the examples of these factors may be "food", "physical exertion", "stress", "glucose reducing drugs", or "supplemental drugs". FIG. 3C shows an example of a user interface, UI screen 302. A factor may be decomposed into further multiple levels of parameters that correlate individually with body glucose response, using a derived overall response for the factor or may not be decomposed into parameters at all, directly correlating with body glucose response, or a combination of both. Information administrator may then input for applicable factors various parameters that may correlate level of glucose response impact with that factor. Examples of such parameters may be for "food", parameters such as "carbohydrate level", "protein level", "glycemic index" etc., for physical exertion parameters such as "cardiovascular activity", "strength training activity" etc. FIG. 3C shows an example of user interface, UI screen 304.

Figure 4D:
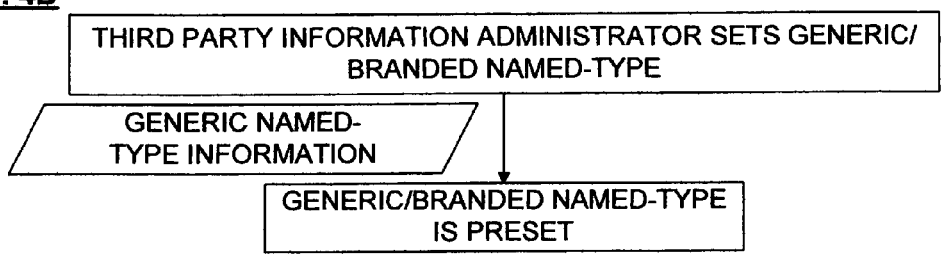
Figure 4E:
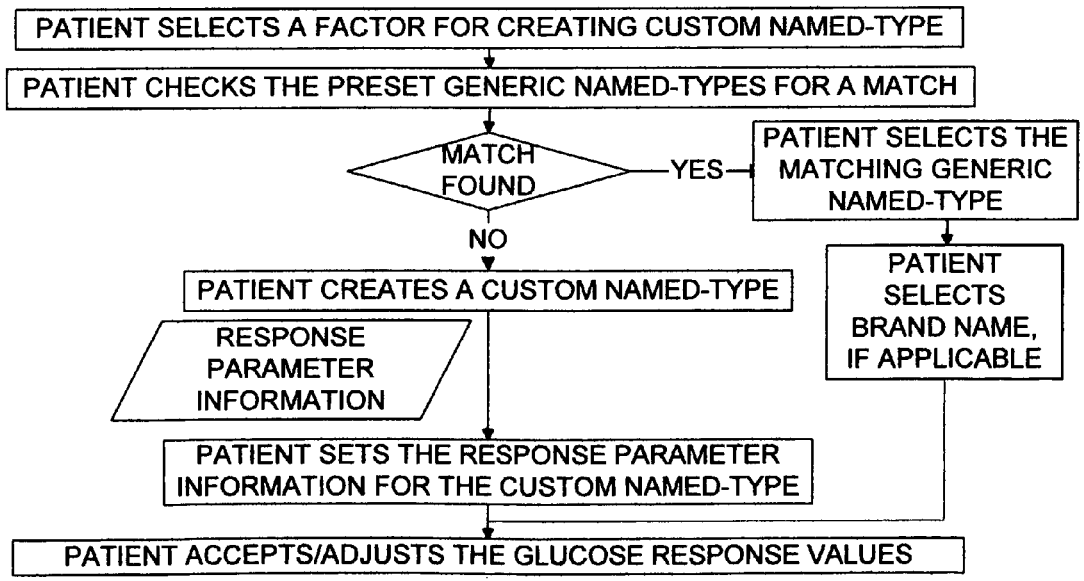

A patient may use patient-computer 130 or patient-device 120 to create custom named-types. A healthcare professional may assist a patient in creating or adjusting custom named-types. Custom named-types are instances for various arbitrary glucose influencing factor types that are relevant for the patient and those that the patient may encounter in daily routine and lifestyle. Invention allows a patient to define these custom named-types in relevance to their glucose influencing properties, track them to a custom level of decomposition or aggregation that is most suitable and convenient for the patient, and receive feedback from the system that enables the patient to improve overall outcomes of the care management program. Invention also enables information administrators that may be third party research institutes or brand owners of common glucose-influencing factors to create pre-set generic named-types that may be used by a patient to form a reliable estimation basis for the custom named-types. FIG. 4A illustrates the components that may be used in a process flow for creating custom and generic named-types. A patient may use correlation parameters between glucose response factors, factor parameters and glucose response estimation such as custom glucose response sensitivity to aid in response estimation. FIG. 4B illustrates the process where patient may utilize and configure correlation parameters for glucose influencing factors, while FIG. 4C shows an example of a user interface, UI screen 402, where a patient may configure glucose sensitivity to various glucose response factors, an example for a factor food being "positive glucose response change of 8 mg/dl for 1 mg of carbohydrate" or for a factor glucose reducing drug being "negative glucose response change of 25 mg/dl for 1 unit of Insulin". Information administrators may create a reliable basis for patients to use for their custom named-type by creating generic named-types. Generic named-types are common named-types that can be preset by information administrators based on their research and credible evidence for average values of glucose response and response parameters. FIG. 4D illustrates a process flow, while FIG. 4E shows an example of a user interface, UI screen 404. In the example for UI screen 404, an information administrator (IA) may select a factor for which IA is creating a generic named-type, input a new or select an existing generic named-type, input a new or select an existing brand for the generic named-type, input a unit quantity and a unit name for the named-type, and input evidence-based glucose response for the generic named-type. UI screen 404 shows average glucose response using response parameters and their evidence-based values. An example of a generic named-type may be "Pasta, dry, enriched", "Spaghetti with Pesto Sauce", "Port Wine", "Orange Juice", "2% Milk", "Running", while an example of branded named-type may be "Tropicana Pure Premium® Orange Juice", "Minute Maid® Orange Juice", "Tae Bo®", or "Novolog®—Insulin". A research institute or a brand owner may create these generic named-types and input respective evidence based parameter values, e.g. parameter value hypothetically may be "16 g Carbohydrate, 80% Glycemic Index for Orange juice" or "12 g Carbohydrate, 50% Glycemic Index for Minute Maid® Orange Juice" or "40% Cardiovascular, 60% Strength Training for Tae Bo®". Response may be input as an overall impact as hypothetically "20% negative glucose response for 1 hour jogging". Response may also be input as average impact at various intervals of time like hypothetically "10% negative impact during first 30 minutes, 20% during next 30 minutes, 5% for 2 hours after ending 1 hour jogging". Response may also be input as a map of impact against time. Patient may use generic named-types as a reliable basis to create and configure custom named-types that are relevant to the patient. FIG. 4F illustrates the process flow for a patient creating a custom named-type, while FIG. 4G shows an example of a user interface, UI screen 406, for the patient to create a custom named-type. A patient may create a custom named-type for an arbitrary glucose-influencing factor that is relevant for the patient. A patient may use one or more preset generic or common named-types as a basis for a new custom named-type and benefit from evidence based measures of a generic named-type to configure the values for the new custom named-type. Example illustrated in UI Screen 506 shows a mechanism for select a generic named-type as a basis for a custom named-type. As illustrated in UI screen 406, a patient may select factor for which the patient is creating a custom named-type, select a generic named-type and brand that is applicable for the custom named-type, input any arbitrary name that is relevant for the patient for the new custom named-type, and enter new or adjust selected generic named-type's glucose response values that are relevant for the patient. System may indicate preset values of glucose response and glucose response parameters from selected generic named-type in assisting patient to form evidence-based reliable basis for configuring glucose response for a named-type. System may also calculate parameter response by using patient's parameter unit correlation factors such as unit glucose sensitivity and parameter unit values. As described earlier, the system may present several mechanisms for a patient to indicate glucose response, a few examples being overall glucose response values, point values at specific time intervals, or a map of glucose response values against time. UI screen 406 shows an example where a patient may indicate glucose response that is relevant for the patient using total response and response at specific time intervals. An example of a custom named-type that is relevant for a patient may be "Home-made Pasta", "Tae Bo® Routine", "Morning Orange Juice", "Novolog®", or "Spring allergies". A patient may select a generic named-type as "Tropicana Pure Premium® Orange Juice" and use the measures as they are for the generic named-type or may adjust it based on several factors that are relevant to the patient's custom type like any other additions like sugar, size of the container etc. A patient may select more than one generic named-type as "Spaghetti with Pesto Sauce" and "Port Wine" to create a custom named-type "Home-made Pasta" and then adjusting the relevant glucose response parameters and values. A healthcare professional may assist a patient in creating, analyzing, or configuring custom named-types. UI screen 408 shows an example where a patient may use combination of generic named factor types to create a custom named factor type.

Figure 5A:
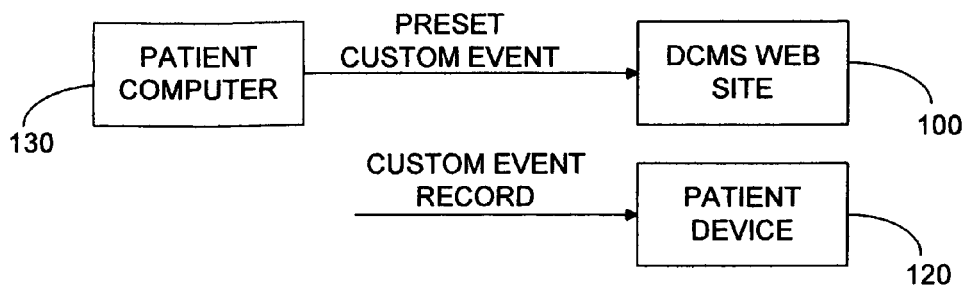
Figure 5B:
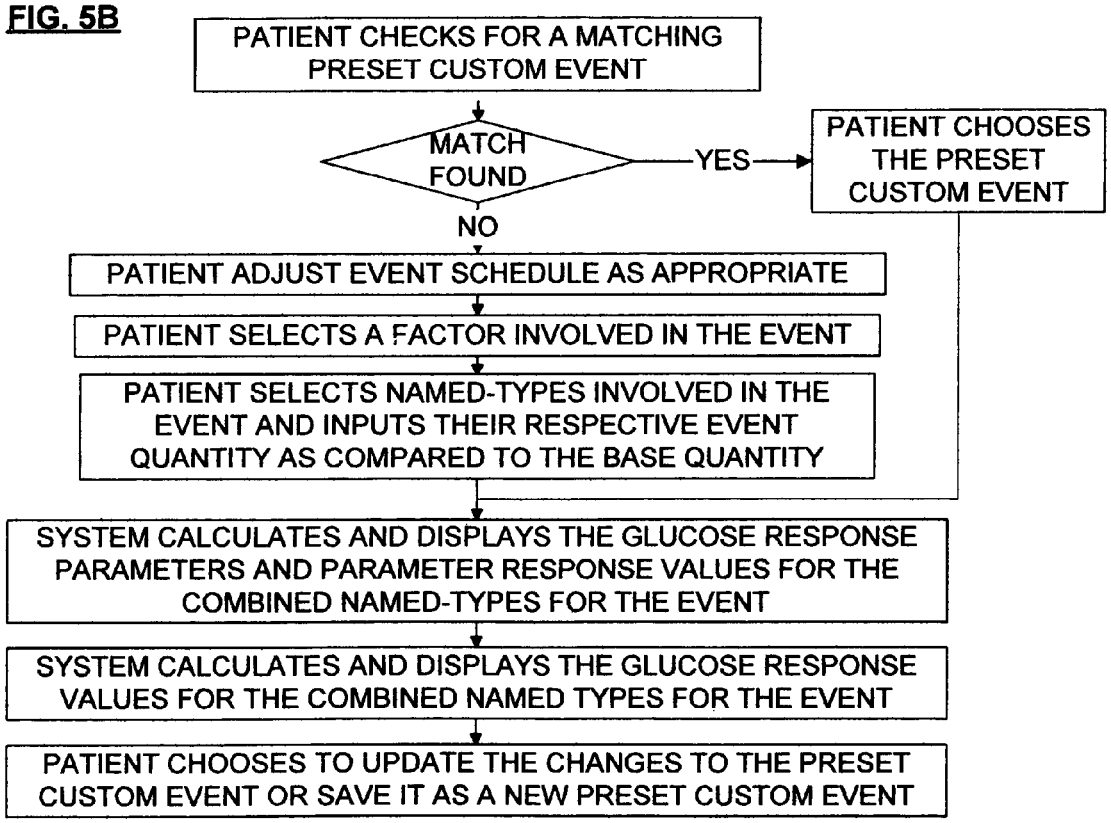
Figure 5C:
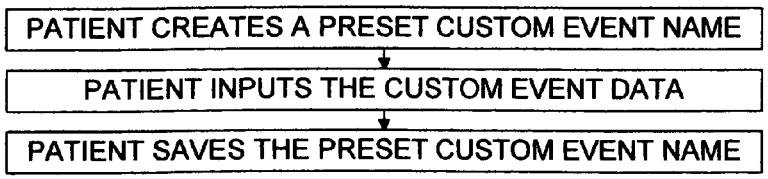

A patient may use patient-device 120 to input ad-hoc or scheduled custom events. A patient may also preset scheduled custom events and may use patient-device 120 or patient-computer 130 create scheduled custom events. A custom event may involve patient's interaction with one or more glucose impacting factors. A patient may input a custom event before, during or after the event. FIGS. 5A, 5B, and 5D illustrate, respectively, a component interaction, a process flow, and an example of a user interface, UI screen 502, for a patient to input a custom event. As illustrated in process flow of FIG. 5B and UI screen 502 of FIG. 5D, a patient may look for a matching custom event that has been preset and involves similar factors as the new event that patient is trying to input. If it is a scheduled custom event and close to the time of patient's data entry, system may highlight or alert the patient for the scheduled preset custom event. For an ad-hoc or arbitrary or custom event, if the patient doesn't find a matching preset custom event, then the patient creates one by selecting involved factors and named-types for the new custom event, entering new or adjusting the system selected event schedule for date and time, and adjusting parameter values and correlation factors, if needed. Named types may be custom named-types, or generic named-types, or mix of both. Based on custom event data for factors, named-types, parameters, and correlation factors, system may calculate and display glucose response. A patient may specify named-type values for the event by "Event Quantity", as shown in FIG. 5D, or by relative portions against "Unit Quantity". As described earlier, the system may present glucose response in various ways that will assist the patient in making any adjustments in the event data, a few examples being total response value, response values at specific intervals, or a map of response values against time. When a matching preset custom event is found, patient may just adjust the preset entries, if needed, simplifying the data entry. An example of a custom event may be "Lunch" that may involve named-types from glucose influencing factors "Food" and "Glucose Reducing Drug" such as "Apple", "Home made Pasta", "Novolog®". A custom event may be modeled both as periodic and non-periodic events. An example of a periodic event may be a particular quantity of basal insulin at a regular frequency i.e. a periodic custom event "Basal Insulin Administration" that may involve glucose influencing factor "Glucose Reducing Drug" and may be set as "0.5 unit quantity of Novolog® every hour every day from 8 AM to 5 PM", and "0.3 unit quantity of Novolog® every hour every day from 5 PM to 8 AM". A custom event may be further modeled as a non-periodic event that may set to alter a previously schedule periodic event". An example of this may be "Evening Jog" that may involve named-types from glucose influencing factor "Physical Exertion" with named-types "Jogging" and previously scheduled periodic event "Basal Insulin Administration" and may set overriding reduced values for the periodic event for certain duration. A patient may choose to save any adjustments made for the new custom event for which a matching preset custom event has been found. UI screen 502 uses a button "Save Preset Event" that the patient may click to save the adjustments for the preset custom event. If a patient enters and an ad-hoc custom event that the patient believes will reoccur in future, then the patient may choose to save it as a preset custom event. FIGS. 5C and 5E illustrate a process flow and an example of a user interface respectively. A patient may invoke UI screen 504, which may be just an extension of UI screen 502, by clicking a button on UI screen 502, "Save Preset Event". The patient, then, may input a name for the preset custom event and scheduling options, if needed. A few examples of scheduling options may be recurring at specific time or day. A healthcare professional may assist a patient in creating, analyzing, or configuring custom named-types. Patient-device 120 may provide an electronic recognition system for inputting a named-type, especially a branded named-type. Information administrator may input a unique identifier for each generic and branded named-type that information administrator owns or has accountability for. The same unique identifier may be encoded on the factor such as a food item that can be electronically recognized by patient-device 120 using any standard electronic recognition systems like bard-code recognition, electromagnetic recognition etc. This may provide a more convenient way for the patient to enter named-type information for a custom event and prevent entry errors.

Figure 6A:
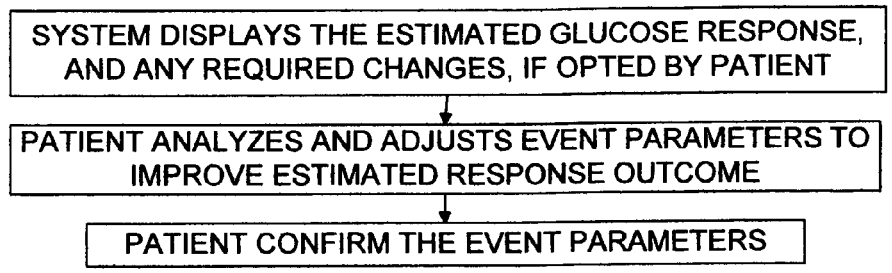
FIGS. 6A-F illustrate the function for event analysis.
Figure 6B:
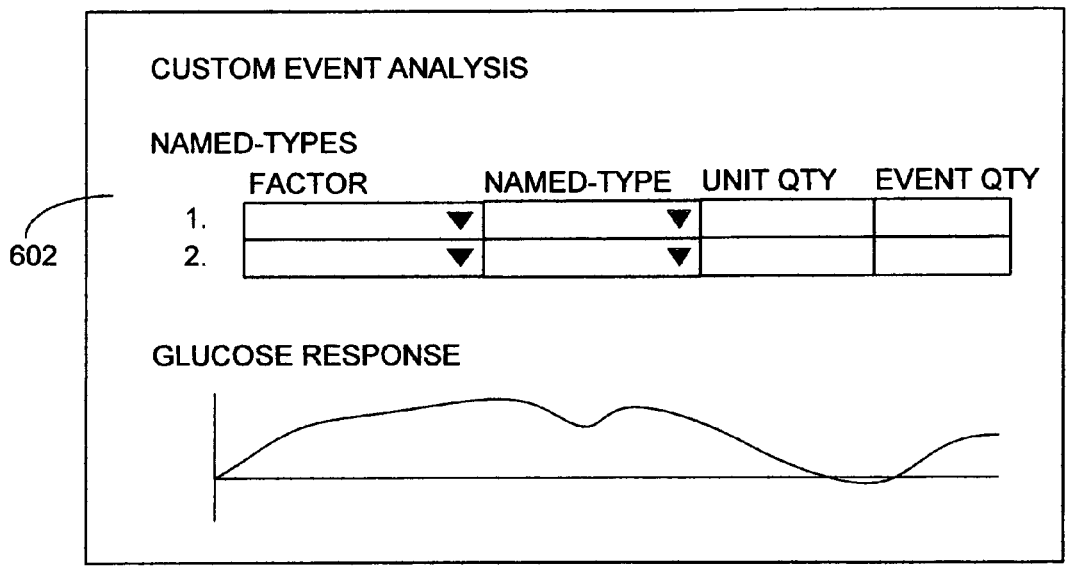
Figure 6C:
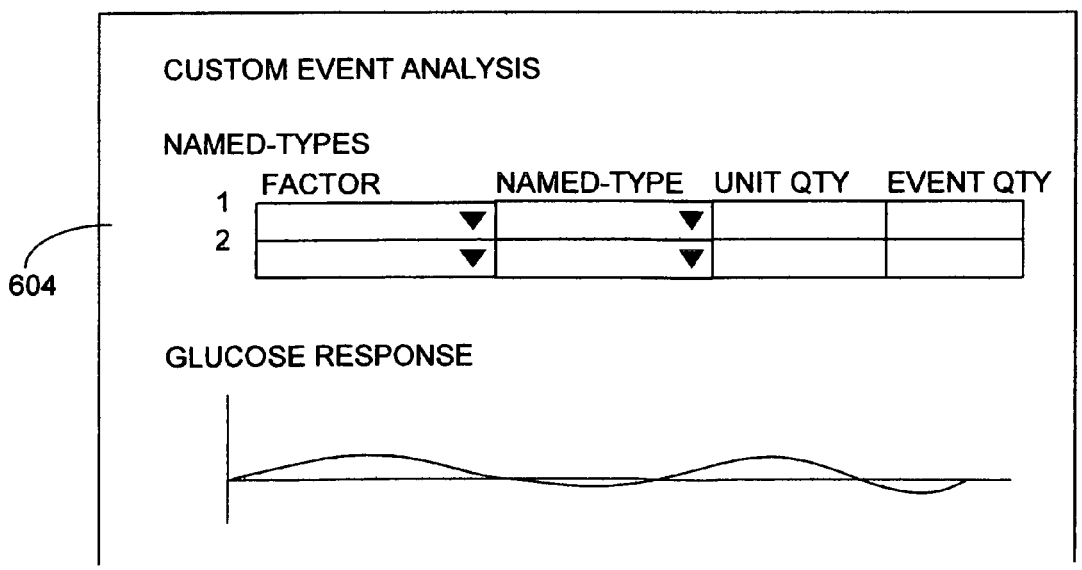
Figure 6D:
Figure 6E:
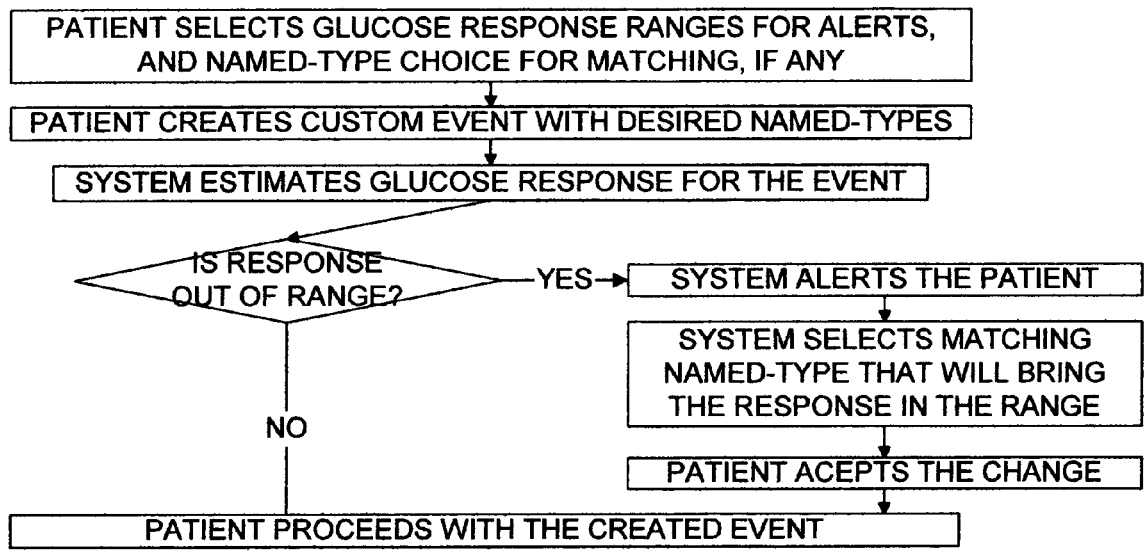
Figure 6F:
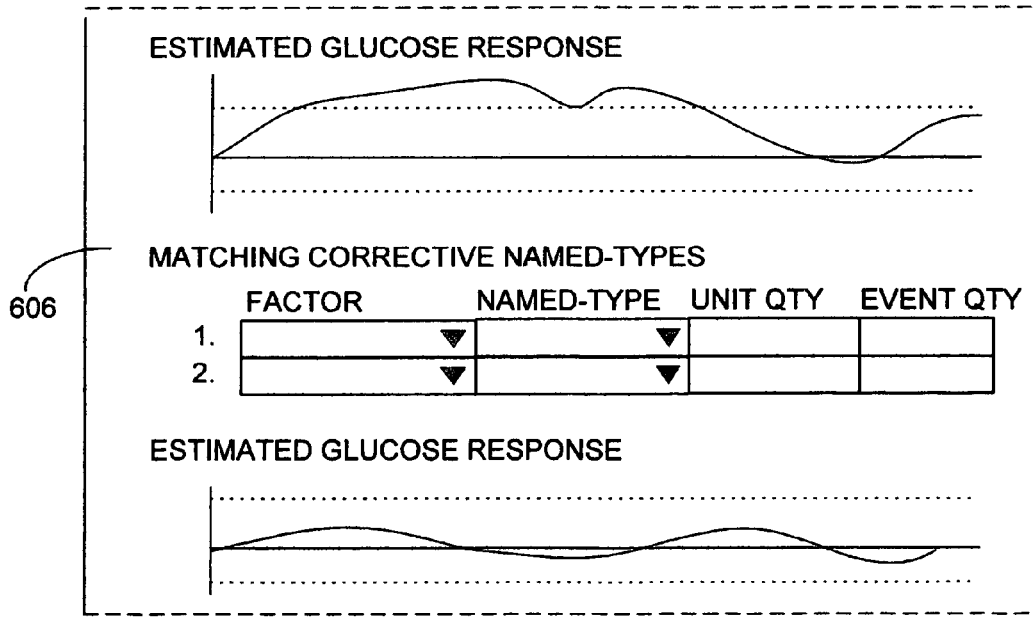

As described earlier, the system may present glucose response for a custom event and a patient may adjust custom event data based on the analysis of the presented response to improve the glucose response outcome for the custom event. FIG. 6A illustrate a process flow where patient analyzes and adjusts a custom event. FIG. 5D shows an example of a user interface where the system shows total glucose response value and glucose response values at specific time intervals. FIGS. 6B and 6C show an example of user interface where system shows map of glucose response values against time for a custom event, which may be presented using interpolation various point values at various times. As the user interfaces UI screen 602 and UI screen 604 show an example of, a patient may analyze glucose response and may choose to adjust the factors to bring the values to desired levels by adjusting the custom event data. UI screen 604 shows an example where a patient may adjust named-type values to bring the higher glucose response values of UI screen 602 closer to desired level as shown in UI screen 604. A patient may set desired levels in terms of a glucose range in terms of point values or values at specific time intervals. A patient may choose system to calculate required changes in named-types for the event to have estimated response within desired levels. A patient may choose named-types or parameters for the named-types used by the system in calculating the change. This way patient can ensure that any changes calculated by the system are practical. FIGS. 6D and 6E illustrates a component interaction and a process flow for setting alerts. FIG. 6F shows an example of a user interface where user sets a low and high value of glucose response for an alert on a custom event. As illustrated in FIG. 6E, a patient may set alert ranges and receive an indication from the system when calculated response is out of the set range. The patient may choose to change the custom event data or select the system to present the corrective options to the patient in order to bring the response back in the range. As illustrated in user interface, UI screen 606, the patient may select one of the desired named-type for system to recommend a corrective value based on the correlation factors. A healthcare professional may assist a patient in creating, analyzing, or configuring preset custom events.

Figures 7A, 7B, 7C:
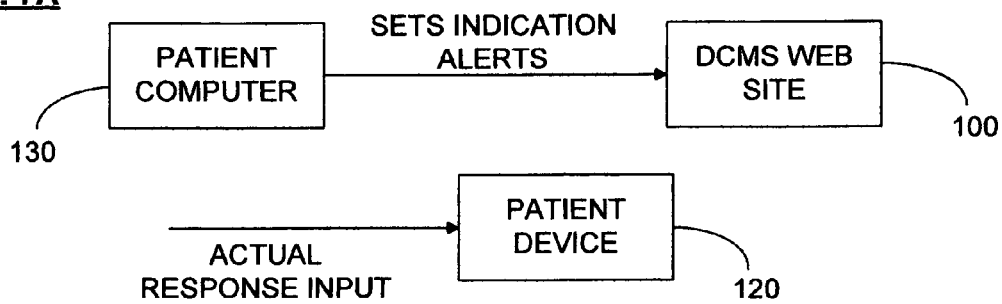
FIGS. 7A-C illustrate the function for response tracking.

A patient may check and input actual body response using patient-device 120 or patient-computer 130. The patient may take this action ad-hoc or in response to an indication of preset alert from the system. FIGS. 7A, 7B, and 7C illustrate a component interaction, a process flow, and an example user interface respectively for an actual glucose response tracking for a patient. Actual response input can be fed to the system manually by the patient or automatically using various glucose testing devices. Standard glucose testing devices may be configured to transmit this data to patient-device 120 or patient-computer 130. The data synchronization can be done in many ways, for example using a wireless or a network wire connection, and on various types of schedules, e.g. real-time upon glucose response check, periodically based on preset configuration, or on request from the patient. As illustrated in user interface, UI screen 702, a patient may manually or automatically input actual body glucose response to the patient-device 120 with date and time of when the glucose response test was performed. A patient also may indicate whether to include this response measure in the analysis by the system, e.g. a patient may choose to exclude the response from the analysis where the patient may feel that it is taken in unusual circumstances or is not representative.

Figure 8A:
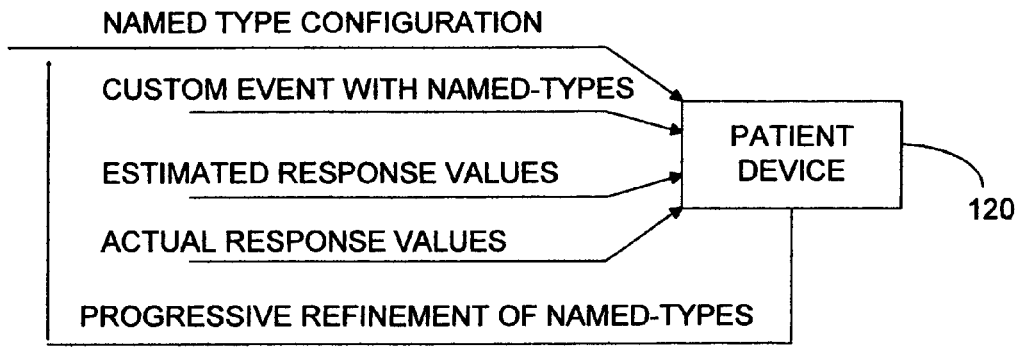
FIGS. 8A-D illustrate the function for progressive refinement by named factor types.
Figure 8B:
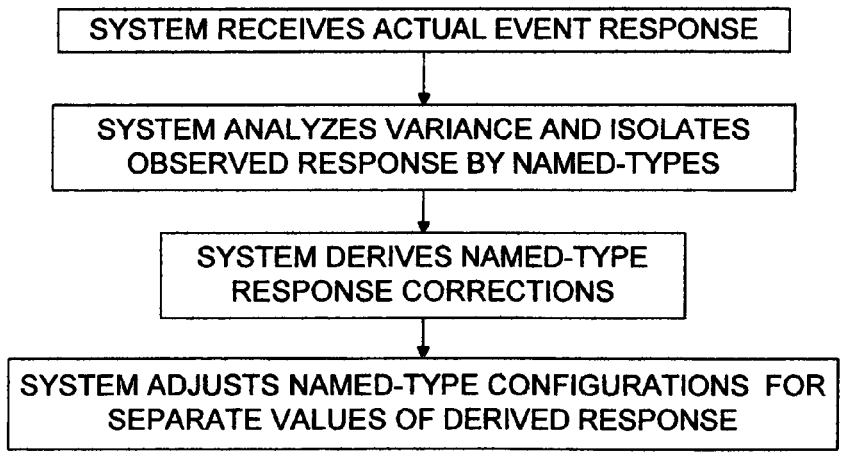
Figure 8C:
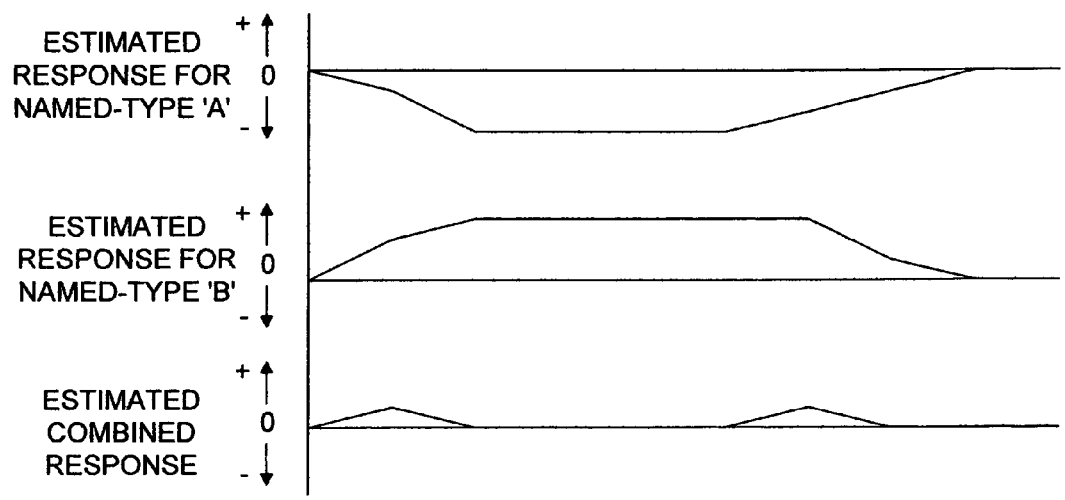
Figure 8D:
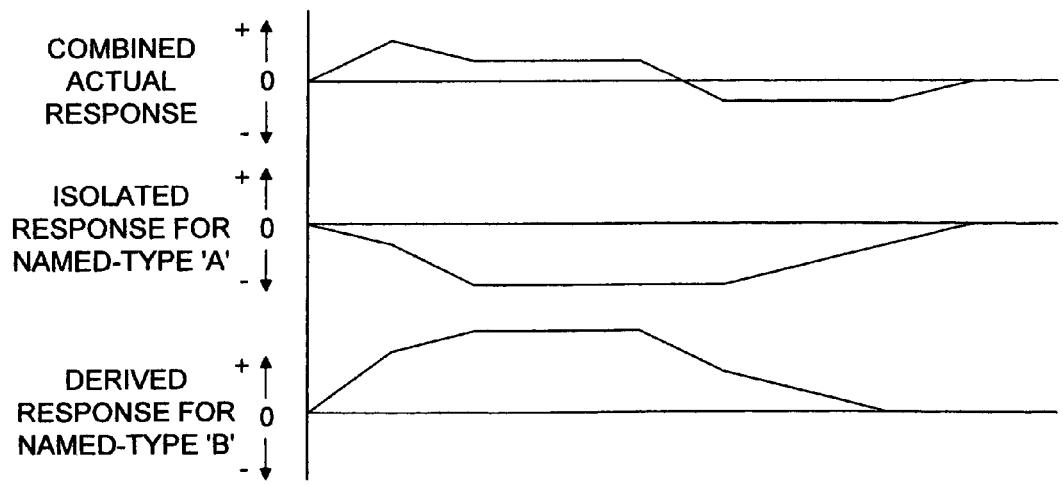

Computer program 106 or computer program 122 may analyze the stored configuration and observational data to adjust the various correlation factor and response parameter values so that variance between a system-calculated and an actual response data can be minimized. This will also give the patient a reliable, evidence-based basis to configure custom events so that event response can be adjusted close to required patient outcome values and improve the overall outcome of the care management program. FIG. 8A illustrates component interaction for this progressive refinement process using patient-device 120 and computer program 122. As described earlier analysis may also be done using computer program 106 as the data is synchronized between patient-device 120 and DCMS Web site 100 or using patient-device 120 in conjunction with DCMS Web site 100. As illustrated in FIG. 8A, patient-device 120 may receive and analyze data from multiple sources like named-type configurations, custom event inputs, input values for correlation factor, input values for response parameters, and actual response values and may create a closed loop system by using progressive refinement of configuration and correlation values to reduce variance between calculated and actual glucose response. It in important to note that the analysis and progressive refinement is performed against specific custom named-types and calculated values are stored separately as derived values from patient configured values for custom named-types. FIG. 8B illustrates a process flow where patient-device 120 may receive an actual event response, computer program 122 may then calculate variance of the actual response against calculated response based on named-type configuration values for the custom event as described earlier, isolate the response values for specific named-types involved in the custom named event, calculate adjustments needed for individual custom named-types, and record the adjusted values separately as derived values. Computer program 122 may further utilize factor parameters and variance of their response to estimate adjustments needed for individual custom named-types or individual factor parameters. In such case, distinct factor parameters may inherit the isolation levels of the named-types or may be attributed isolation levels of their own. FIGS. 8C and 8D illustrate a process of isolation response values using a hypothetical example. FIG. 8C shows a custom event with two hypothetical named-types, "Type A" and "Type B" and shows configured glucose response maps individually. FIG. 8C also illustrates glucose response map of the custom event with equal weight from both named-types, "Type A" and "Type B". FIG. 8D shows the actual response input as entered by the patient against specific time intervals and interpolated to derive a map. Various isolation techniques may be used in deriving response for individual named-types from the actual response. In this case, FIG. 8 D uses a confidence level based approach with higher confidence level for named-type "Type A", and derives response for named-type "Type B" by subtracting the response levels for each observed point. In confidence level approach, confidence levels can be tracked for a named-type on a weighted scale of observed variance measure with variance measures calculated for each actual response that involves the specific named-type. Discrete measurements and error tracking for named factor type responses at various time intervals allow for isolation techniques such as attributing confidence levels to discrete factor type responses and setting a specific confidence level for error identification. System may further calculate the correlation and response parameter values of configured data for further refinement. Computer program 122 may use various standard statistical models for analyzing and isolating the named-type configuration and correlation values, an example being standard analysis of variance (ANOVA) model. Computer program may also use mathematical equations to calculate the configuration and correlation factors for specific named-type. A hypothetical example is given below for illustration of one of the methods:

Factor Setup: An information administrator sets factors as "Food" and "Glucose Reducing Drug" with factor parameters for "Food" as "Carbohydrates" and for "Glucose Reducing Drug" as "Insulin".

Factor Parameter Setup: A patient sets factor parameter correlations as glucose sensitivity—"Positive 3.125 mg/dl for 1 g of Carbohydrates" and "Negative 25 mg/dl for 1 unit of Insulin".

Generic Named-Type Setup: The information administrator then creates generic named-types as "Apple" with factor parameter as "Carbohydrate 16 g" and "Pasta" with factor parameter as "Carbohydrate 24 g".

Custom Named-Type Setup: The patient then creates custom named-types as "Apple" with factor parameter as "Carbohydrates 16 g", "Home made Pasta" with "Carbohydrates 32 g", and "Novolog®" with "100% Insulin Response".

Custom Event: The patient then inputs a custom event "Breakfast" with named-types as "Apple" with "1 unit quantity" and "Novolog®" with "2 unit quantity". The patient checks the event analysis and proceeds with it, as the outcome of glucose response is no significant change in total glucose response and is acceptable.

Response: On system alert at a specific time interval, the patient checks and records the actual response to the event as "Negative 10 mg/dl"

Custom Event: The patient then enters another event "Lunch" with named-types as "Apple" with "½ unit quantity", "Home made Pasta" with "1 unit quantity", and "Novolog®" with "4 unit quantity. The event analysis indicates that overall response for the event will be "Positive 25 mg/dl", which is not acceptable to the patient and hence on system recommendation the patient adjusts the named-type "Novolog®" to "5 unit quantity". With the adjustment, the outcome of glucose response is no significant change in total glucose response and is acceptable.

Response: On system alert at a specific time interval, the patient checks and records the actual response to the event as "Positive 25 mg/dl"

Custom Event: The patient then enters yet another event "Dinner" with named-types as "Apple" with "1 unit quantity", "Home made Pasta" with "1 unit quantity", and "Novolog®" with "6 unit quantity. The patient checks the event analysis and proceeds with it, as the outcome of glucose response is no significant change in total glucose response and is acceptable.

Response: On system alert at a specific time interval, the patient checks and records the actual response to the event as "Positive 20 mg/dl"

Progressive Refinement: System determines the variance in the glucose response to named-types and records "Derived Glucose Response" to "Apple" is "Positive 50 mg/dl" against "Custom Glucose Response" which is "Positive 50 mg/dl", "Derived Glucose Response" to "Pasta" is "Positive 150 mg/dl" against "Custom Glucose Response" which is "Positive 100 mg/dl", "Derived Glucose Response" to "Novolog®" is "Negative 30 mg/dl" against "Custom Glucose Response" which is "Negative 25 mg/dl". System may further decompose the variance to response parameters and correlation factors and determine that derived carbohydrate content for "Home made Pasta" is "48 g" instead of "32 g" as estimated by the patient, while glucose sensitivity for "Novolog®" is "Negative 30 mg/dl per unit quantity" as opposed to "Negative 25 mg/dl per unit quantity"

One of the methods using mathematical linear equation analysis may be:

Assuming variables as
Apple—Quantity: "$Q_a$", Glucose Response: "$G_a$"
Home made Pasta—Quantity: "$Q_p$", Glucose Response: "$G_p$"
Novolog®—Quantity: "$Q_n$", Glucose Response: "$G_n$"
Event—Glucose Response: "Ge"
Then, overall response may be $$Q_a \cdot G_a + Q_p \cdot G_p + Q_n \cdot G_n = G_e$$

$$1 \cdot G_a + 0 \cdot G_p + 2G_n = -10$$

$$\tfrac{1}{2} \cdot G_a + 1 \cdot G_p + 5G_n = 25$$

$$1 \cdot G_a + 1 \cdot G_p + 6G_n = 20$$

Solving the linear equations we get derived glucose response for named-types as
$G_a$=50 mg/dl
$G_p$=150 mg/dl
$G_n$=−30 mg/dl Considering the confidence level analysis based on number of such results as higher confidence level for glucose sensitivity for response parameter carbohydrates and lower confidence level for glucose sensitivity for Novolog®, we get Carbohydrates for "Home made Pasta" as 48 g (150/3.135)
Glucose Sensitivity for "Novolog®" as −30 mg/dl per unit quantity or 120% of "Insulin" glucose sensitivity Another method for variance analysis using a standard linear regression analysis with the following data may be:

| $Q_a$ | $Q_p$ | $Q_n$ | $G_e$ |
|---|---|---|---|
| 1.0 | 0.0 | 2 | −10 |
| 0.5 | 1.0 | 5 | 25 |
| 1.0 | 1.0 | 6 | 20 |
| 1.0 | 0.0 | 2 | −10 |
| 1.0 | 1.0 | 6 | 20 |
| 2.0 | 0.5 | 6 | −5 |

Regression Analysis: $G_e$ versus $Q_p$, $Q_n$, $Q_a$
$Q_a$ is highly correlated with other X variables
$Q_a$ has been removed from the equation
The regression equation is $G_e$=0.000000+50.0 $Q_p$−5.00 $Q_n$

| Predictor | Coefficient | SE Coefficient | T | P |
|---|---|---|---|---|
| Constant | 0.00000000 | 0.00000000 | * | * |
| $Q_p$ | 50.0000 | 0.0000 | * | * |
| $Q_n$ | −5.00000 | 0.00000 | * | * |

S=0 R−Sq=100.0% R−Sq(adj)=100.0%
Analysis of Variance

| Source | DF | SS | MS | F | P |
|---|---|---|---|---|---|
| Regression | 2 | 1383.33 | 691.67 | * | * |
| Residual Error | 3 | 0.00 | 0.00 | | |
| Total | 5 | 1383.33 | | | |

Using the variance analysis, we get that derived $G_p$ as +100 mg/dl+50 mg/dl=+150 mg/dl, where 50 mg/del is positive variance from current glucose response of "Home made Pasta" and $G_n$ as −25 mg/dl−5 mg/dl=−30 mg/dl, where 5 mg/dl is negative variance from current glucose response for "Novolog®"

A patient may update custom configurations such as glucose response value, parameters, and any correlation factors by specific named-types to improve accuracy of response estimation resulting in improvement of overall outcome of the care management program. FIGS. 9A and 9B illustrate a component interaction and a process flow respectively. A patient may use patient-computer 130 or patient device 120 to review and update configuration information. Data may be used independently on patient-device 120 or may be synchronized between patient-device 120 and DCMS Web site 100 and vice versa. As illustrated in FIG. 9B, patient reviews the configuration and response variance information for various named-types. System may recommend certain named-types that have higher variance or higher impact on the outcome. FIG. 9C shows an example of a user interface, UI screen 902, for reviewing and updating a named-type configuration. UI screen 902 shows three different categories of values, Generic, Custom, and Derived, based on prior configurations and data analysis. Generic values are the ones based on generic named-types that are not adjusted or customized by a patient. Custom values are adjusted values by patient based on relevance of the values for the patient. Derived values are calculated and stored values based on earlier described progressive refinement of named-types process from observed and isolated actual response values. A patient may select a named-type and a patient may adjust custom values to reduce the variance of the custom values that are used for custom named-type in a custom event against actual response to the custom event and the custom named-type.

ADVANTAGES

From the description above, a number of advantages of the present invention become evident:

a) Present invention enables a patient to estimate arbitrary type of factors. It enables recording these types, estimating them, and tracking them against the estimations. It enables the patient to form a consistent basis for these factors by recording and tracking their parameters and in more complex types their composition of other such types. It enables the patient to track response to a mix of arbitrary factor types clearly and estimate expected change in glucose response. It enables the patient to isolate errors amongst a mix of input factors by mechanism of tracking arbitrary named-types, their composition, and their expected and observed responses in various scenarios. This allows the patient to form and improve estimations for arbitrary type of factors relevant for the patient instead of relying on intuition or approximation. The improved estimation accuracy results in reduced variation in glucose response level and improved patient health.

b) The invention not only presents a systematic method of reducing estimation errors in glucose response to an arbitrary factor type but also tracking and isolating errors between the relative strength and the unit response sensitivity of the factor and the factor parameters. It enables the patient to track the unit response sensitivity of common factor parameters amongst different factor types. This allows use of isolation techniques as explained in the operation earlier to isolate errors between relative strength and the unit response sensitivity which would have been otherwise highly complex for a patient to do manually. This results in better and simpler estimation for the patient improving resulting outcome. Since, the invention enables tracking of arbitrary factor types and factor type parameters uniquely, augmenting or canceling responses for these can be easily tracked by the system and any human errors are avoided.

c) The invention enables the patient to utilize a mix of multiple factor types to restore the blood glucose level. It takes into account varying impacts of input factor types in determining the most appropriate corrective action to an estimated glucose response change. It presents the patient not only with a most effective solution but also a practical one by allowing the patient to choose available input factor types amongst which system can choose the most appropriate mix of input factors.

d) The invention enables recording clear cause-effect tracking in terms of estimated changes, observed behavior, corrective changes, and resulting response change. This enables the patient or a patient healthcare administrator to analyze the improvements and choosing the right course of action. Additionally, the invention enables the use of statistical analysis and correction methods that remove the compounding effect of mistakes in corrective steps.

e) The invention utilizes a continuous feedback system, discrete measurements, and statistical error correction mechanisms such as rolling estimate averages. This creates a continuous error reduction system and enables the patient to reduce estimation errors due to circumstantial and unforeseen changes. This improves the overall outcome response accuracy.

f) The invention enables a patient to track arbitrary factors that promotes a flexible lifestyle for the patient. It also enables the patient to track and correct errors in relative portions or strengths of arbitrary and standardized factor types. So, now the patient can track, isolate, and track errors in any of these factor types consistently. This reduces the response variations.

g) The invention provide a much better alternative to static reports by enabling dynamic tracking of arbitrary factor types, their parameters, estimated and observed response, corrective actions, and improvement. It provides a systematic method to patient or patient's healthcare administrator to improve treatment outcome consistently and continuously.

h) The invention provide a much better alternative to static reports by enabling dynamic tracking of arbitrary factor types, their parameters, estimated and observed response, error correlations, corrective actions, and correlated improvements. It provides a systematic method to patient or patient's healthcare administrator to improve treatment outcome consistently and continuously.

i) The invention creates a systematic record of trackable factor types, events, and correlated responses and corrective actions. This enables not only the patient, but also patient's healthcare administrator to review and analyze the treatment error and improvements.

j) The invention offers a cost-effective and non-intrusive solution for proactive treatment improvements and reducing the risk of costly and potential life threatening complications.

k) The invention enables the patient to choose named factor types from 3rd party resources that may be consistent with patient's needs.

l) The invention enables the patient to prevent any input errors by utilizing automated recognition means such as electronic recognition of standard or branded named factor types.

CONCLUSIONS, RAMIFICATIONS, AND SCOPE

Although the description above contains many specifications, these should not be construed as limiting the scope of the invention but as merely providing illustrations of some of the presently preferred embodiments of this invention. The scope of the invention should be determined by the appended claims and their legal equivalents, rather than by the examples given.

I claim:

1. A method for improving a chronic care treatment outcome, comprising the steps of:
   (a) recording identification information for a plurality of users;
   (b) recording for each of said users, a treatment outcome and, a plurality of arbitrary factors, where said arbitrary factors are relevant for each of said users and are correlated with said treatment outcome;
   (c) recording for each of said users, a plurality of arbitrary types of said factors relevant for said user and recording for each said arbitrary type, an arbitrary name, a unit, and a correlation with said treatment outcome, where said correlation is as estimated by user;
   (d) recording for each of said users, a plurality of arbitrary events impacting said treatment outcome and recording for each said arbitrary event, a plurality of said arbitrary types identified by said arbitrary type name and for each said arbitrary type, a relative strength as compared to said arbitrary type unit, where said relative strength is as estimated by user;
   (e) computing for each of said users, a change estimate in said treatment outcome at any arbitrary time and computing an error in said outcome change estimate, where said outcome change estimate is due to said correlation of said arbitrary types relevant at said arbitrary time, and where said error in outcome change estimate is result of an error in change estimate by said arbitrary type when said outcome change estimate is compared to an observed change at said arbitrary time;
   (f) computing for each of said arbitrary types for each of said users, an error in said correlation, where said correlation is as estimated by said user, and where said error attributable to said arbitrary type is isolated by correlating a plurality of said treatment estimation errors where said arbitrary type is relevant;

wherein the chronic care treatment may be a blood glucose control treatment for a Diabetic patient and the treatment outcome is a resulting acceptable value of blood glucose level for said patient;

wherein said user for the step of recording said identification information may be a patient, or a healthcare advisor, or an assistant, where said healthcare advisor, and said assistant may be permitted by said patient to access information about said patient, and may assist said patient in configuring, analyzing and recording said patient's information;

wherein the step of recording a plurality of said factors includes recording for each factor a plurality of factor parameters, and for each said factor parameter a name, a unit, and a correlation with said treatment outcome, where said plurality of factor parameter may be correlated with said treatment outcome, and where said correlation may be as estimated by user, and wherein the step of computing said error in said correlation for said arbitrary type includes computing for each of said factor parameters of said arbitrary type, an error in said correlation of said factor parameter, where said error in said correlation of said factor parameter may be isolated by correlating a plurality of said treatment estimation errors where said arbitrary type may be relevant.

2. A method according to claim 1 wherein the step of recording of said correlation of said arbitrary type includes a confidence value, where said confidence value indicates estimated confidence of accuracy of said arbitrary type correlation, and where said confidence value is used to isolate said error in said correlation of said arbitrary type.

3. A method according to claim 1 wherein the step of recording of said correlation for each said arbitrary type includes recording of correlation at a plurality of discrete time intervals.

4. A method according to claim 1 comprising the step of: recording for said user, a plurality of common types of said factors relevant for a general user population and recording for each said common type, a name, a unit, and a correlation with said treatment outcome, and wherein the step of recording for each said arbitrary event, includes a plurality of said common types identified by said common type name and for each said common type, a relative strength compared to said type unit.

5. A method according to claim 4 wherein the step of recording for each said arbitrary type includes a correlation to a plurality of said common types, where said correlation to a plurality of said common types is used to determine said correlation of said arbitrary type.

6. A method according to claim 4 wherein the step of recording of plurality of common types includes recording for each an identification of an entity, where said entity provides said recording of plurality of common types, and comprising the step of:
allowing said user to select said common type associated with said entity.

7. A method according to claim 6 wherein the step of recording of plurality of common types includes recording for each said common type, an identification of a brand associated with said common type and comprising the step of:
allowing said user to select common type associated with said brand.

8. A method according to claim 7 comprising the step of: associating said common type identified with said brand with a unique code and identifying said common type in said arbitrary event by a means to recognize said unique code for said common type identified with said brand.

9. A method according to claim 1 comprising the step of: recording said arbitrary event as a preset event for repetitive use and recording a time schedule for repetitive occurrence of plurality of said preset events.

10. A method according to claim 1 wherein the step of computing said error in said correlation includes computing an error in said relative strength of said arbitrary type, where said error attributable to said arbitrary type is isolated by correlating a plurality of said treatment estimation errors where said arbitrary type is relevant.

11. A method according to claim 1 comprising the step of: recording a plurality of said estimation errors in said correlation and selecting most relevant of said plurality of said estimation errors to compute a correction in said user estimated correlation.

12. A method according to claim 11 comprising the step of: allowing said user to selectively accept said error in said correlation.

13. A system for improving a chronic care treatment outcome comprising a non-transitory computer processor usable medium accessible comprising:
(a) a computer processor readable program embodied therein recording an identification information for a plurality of users;
(b) a computer processor readable program embodied therein recording for each of said users, a treatment outcome and, a plurality of arbitrary factors, where said arbitrary factors is relevant for each of said users and is correlated with said treatment outcome;
(c) a computer processor readable program embodied therein recording for each of said users, a plurality of arbitrary types of said factors relevant for said user and recording for each said arbitrary type, an arbitrary name, a unit, and a correlation with said treatment outcome, where said correlation is as estimated by user;
(d) a computer processor readable program embodied therein recording for each of said users, a plurality of arbitrary events impacting said treatment outcome and recording for each said arbitrary event, a plurality of said arbitrary types identified by said arbitrary type name and for each said arbitrary type, a relative strength as compared to said arbitrary type unit, where said relative strength is as estimated by user;
(e) a computer processor readable program embodied therein computing for each of said users, a change estimate in said treatment outcome at any arbitrary time and computing an error in said outcome change estimate, where said outcome change estimate is due to said correlation of said arbitrary types relevant at said arbitrary time, and where said error in outcome change estimate is result of an error in change estimate by said arbitrary type when said outcome change estimate is compared to an observed change at said arbitrary time; and
(f) a computer processor readable program embodied therein computing for each of said arbitrary types for each of said users, an error in said correlation, where said correlation is as estimated by said user, and where said error attributable to said arbitrary type is isolated by correlating a plurality of said treatment estimation errors where said arbitrary type is relevant.

* * * * *